(12) United States Patent
Berndt

(10) Patent No.: US 9,304,141 B2
(45) Date of Patent: Apr. 5, 2016

(54) METHOD AND APPARATUS FOR DETERMING DISPENSE VOLUME

(75) Inventor: Klaus W. Berndt, Cockeysville, MD (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 1224 days.

(21) Appl. No.: 12/596,079

(22) PCT Filed: Apr. 18, 2008

(86) PCT No.: PCT/US2008/060763
§ 371 (c)(1),
(2), (4) Date: Jun. 3, 2010

(87) PCT Pub. No.: WO2008/131186
PCT Pub. Date: Oct. 30, 2008

(65) Prior Publication Data
US 2010/0241370 A1    Sep. 23, 2010

Related U.S. Application Data

(60) Provisional application No. 60/912,576, filed on Apr. 18, 2007.

(51) Int. Cl.
*G01F 1/20*    (2006.01)
*G01F 1/05*    (2006.01)
(Continued)

(52) U.S. Cl.
CPC .................. *G01N 35/1016* (2013.01)

(58) Field of Classification Search
CPC .................................... F01N 35/1016
USPC ............. 702/19, 20, 47, 50, 55, 85, 104, 134, 702/137; 29/525; 422/100; 436/150
See application file for complete search history.

(56) References Cited

U.S. PATENT DOCUMENTS 4,106,911 A    8/1978  Marcelli
4,107,658 A    8/1978  Hill et al.
(Continued)

FOREIGN PATENT DOCUMENTS

EP    0164679 A2    12/1985
EP    0355791 A2    2/1990
(Continued)

OTHER PUBLICATIONS

International Search Report and Written Opinion for Application No. PCT/US2008/060763 dated Jul. 8, 2008.

*Primary Examiner* — Gregory J Toatley
*Assistant Examiner* — Felix Suarez
(74) *Attorney, Agent, or Firm* — Lerner, David, Littenberg, Krumholz & Mentlik, LLP

(57) ABSTRACT

In needle-based dispensing systems, the target amount of liquid to be dispensed is in many cases very well controlled. However, the amount of liquid that is actually reaching the receiving well may show a discrepancy, because part of the liquid leaving the inner needle space remains on the outer surface of the dispense needle, and so a small amount of liquid is "lost" in the dispensing act. A sensor arrangement according to the present invention is suitable for detecting the presence of any liquid from the aspiration reservoir that is left behind on the outside of the dispense needle, before the dispense step is actually started. The "lost" volume can also be measured very accurately by inserting the tip of a dispense needle into a hollow metallic cylinder, forming a capacitor, whereby the capacitance value depends on the volume of the "lost" dispense volume.

36 Claims, 20 Drawing Sheets

(51) Int. Cl.
  *G01F 1/22* (2006.01)
  *G01F 1/32* (2006.01)
  *G01N 35/10* (2006.01)

(56) References Cited

U.S. PATENT DOCUMENTS

| | | | |
|---|---|---|---|
| 4,196,615 A | 4/1980 | Davis | |
| 4,417,473 A | 11/1983 | Tward et al. | |
| 4,818,492 A | 4/1989 | Shimizu | |
| 5,304,347 A | 4/1994 | Mann et al. | |
| 5,601,980 A | 2/1997 | Gordon et al. | |
| 5,855,851 A * | 1/1999 | Matsubara et al. | 422/511 |
| 5,960,530 A * | 10/1999 | Kerr et al. | 29/525 |
| 6,029,896 A | 2/2000 | Self et al. | |
| 6,092,422 A * | 7/2000 | Binnig et al. | 73/651 |
| 6,148,666 A | 11/2000 | Roesicke | |
| 6,213,354 B1 | 4/2001 | Kay | |
| 6,244,214 B1 * | 6/2001 | Hebrank | 119/6.8 |
| 6,551,558 B1 | 4/2003 | Mann et al. | |
| 6,749,740 B2 * | 6/2004 | Liamos et al. | 205/792 |
| 6,823,730 B2 | 11/2004 | Buck et al. | |
| 6,851,778 B2 | 2/2005 | Okuda | |
| 6,875,404 B2 | 4/2005 | Hirota et al. | |
| 7,125,727 B2 * | 10/2006 | Massaro | 436/180 |
| 7,199,594 B2 * | 4/2007 | Kermani | 324/663 |
| 7,337,662 B2 * | 3/2008 | Sato et al. | 73/304 C |
| 7,416,706 B2 * | 8/2008 | Brunner et al. | 422/106 |
| 7,439,072 B2 * | 10/2008 | Shvets et al. | 436/150 |
| 7,735,354 B2 * | 6/2010 | Yamamoto et al. | 73/61.41 |
| 7,896,197 B2 * | 3/2011 | Furey et al. | 222/64 |
| 7,916,299 B2 * | 3/2011 | Trump et al. | 356/440 |
| 7,959,863 B2 * | 6/2011 | Yamamoto et al. | 422/68.1 |
| 7,992,437 B2 * | 8/2011 | Tshishiku | 73/431 |
| 8,057,756 B2 * | 11/2011 | Londo et al. | 422/501 |
| 2001/0016177 A1 | 8/2001 | Pelc et al. | |
| 2003/0175163 A1 * | 9/2003 | Shvets et al. | 422/100 |
| 2003/0215957 A1 | 11/2003 | Lemmo et al. | |
| 2004/0087031 A1 * | 5/2004 | Simon, Jr. | 436/100 |
| 2004/0101445 A1 * | 5/2004 | Shvets et al. | 422/100 |
| 2005/0223814 A1 | 10/2005 | Shvets | |
| 2010/0028213 A1 | 2/2010 | Gorka | |

FOREIGN PATENT DOCUMENTS

| | | |
|---|---|---|
| EP | 0505004 A2 | 9/1992 |
| EP | 0725267 A2 | 8/1996 |
| EP | 1607747 | 12/2005 |
| EP | 1785731 | 5/2007 |
| JP | 53-9194 | 1/1978 |
| JP | 62-218818 | 9/1987 |
| JP | 01-178836 | 7/1989 |
| JP | 07-027770 | 1/1995 |
| JP | 08-146011 | 6/1996 |
| JP | 10-038899 | 2/1998 |
| JP | 10-114394 | 5/1998 |
| JP | 2004251818 A | 9/2004 |
| JP | 2006-003365 | 1/2006 |
| JP | 2006058188 A | 3/2006 |
| JP | U-3121828 | 5/2006 |
| JP | 2007-139767 | 6/2007 |
| WO | 9809151 A1 | 3/1998 |
| WO | 0051736 A1 | 9/2000 |
| WO | 0189694 A1 | 11/2001 |
| WO | 0226499 A1 | 4/2002 |
| WO | 03106936 A2 | 12/2003 |
| WO | 2008055757 A1 | 5/2008 |
| WO | 2009122082 | 10/2009 |

* cited by examiner

METHOD AND APPARATUS FOR DETERMING DISPENSE VOLUME

FIELD OF THE INVENTION

The present invention relates to methods and apparatus for identifying and quantifying volume loss during the dispensing of a liquid into a container.

BACKGROUND OF THE INVENTION

The dispensing of liquid reagent droplets of small volume with high accuracy represents an essential process step in the production of medical diagnostic assays. These assays are often based on two-dimensional arrays of open wells, such as microtiter plates. Some examples of such dispensing systems are described in the following references; U.S. Pat. No. 4,107,658, U.S. Pat. No. 4,196,615, U.S. Pat. No. 4,417,473, U.S. Pat. No. 4,818,492, U.S. Pat. No. 5,304,347, U.S. Pat. No. 5,601,980, U.S. Pat. No. 6,029,896, U.S. Pat. No. 6,148,666, U.S. Pat. No. 6,213,354, U.S. Pat. No. 6,551,558, U.S. Pat. No. 6,823,730, U.S. Pat. No. 6,851,778, U.S. Pat. No. 6,875,404, US 2001/0016177 A1, WO 98/09151, WO 00/51736, WO 01/89694 A1, WO 02/26499 A1, WO 03/106936, EP 0,164,679, EP 0,355,791, EP 0,505,004, EP 0,725,267, JP 2004251818 A, and JP 2006058188 A.

However, the accurate determination of the volume for individual dispensed droplets still remains a problem.

It has been found that, in needle-based dispensing systems, the target amount of liquid that is leaving the inner needle space is in many cases very well controlled, e.g., by the specific motion of a dispensing piston. The amount of liquid that is actually reaching the receiving well may show irregularities, however, because part of the liquid leaving the inner needle space is creeping along the outer diameter of the dispense needle, and is thereby forming an amount of liquid that is "lost" in the particular dispensing act. This mechanism may repeat itself in one or more successive dispensing acts and a substantial amount of liquid may accumulate, therefore, on the outer needle diameter. Once a critical amount of liquid has been accumulated, this liquid will "join" a dispensed droplet, generating an actual dispensed volume that by far exceeds the target dispense volume.

Therefore an apparatus and method is required for an accurate determination of the actual dispensed volume for individual dispensed droplets.

SUMMARY OF THE INVENTION

Pursuant to the embodiments of the present invention, an accurate determination of the actual dispensed volume for individual dispensed droplets is achieved by measuring the part of the dispensed target volume that is "lost" and remains on the outer side of a dispense needle after a liquid has been dispensed. Assuming that the target volume of liquid leaving the inner space of the needle is well-controlled, the actual volume of dispensed liquid reaching a well can then be determined by subtracting the "lost" volume from the target volume. It has been found that the "lost" volume can be measured very accurately by inserting the tip of a dispense needle into a hollow metallic cylinder, forming a substantially concentric cylinder capacitor, whereby the capacitance value depends on the volume of the "lost" dispense volume remaining on the outer side of a dispense needle after a liquid has been dispensed.

Various embodiments of the present invention provide a dispense volume sensor for determining the volume of a dispensed liquid sample. According to one embodiment, a dispense volume sensor includes a dispense needle for dispensing a liquid sample and a receiving cylinder for receiving the dispense needle wherein a capacitor is formed upon receipt of the dispense needle by the receiving cylinder. The measured capacitance of the capacitor is substantially independent of the dielectric constant of a material that is present on an outside surface of the needle tip.

In another embodiment a dispense volume sensor is provided having a plurality of dispense needles each having a needle tip arranged in an array of at least one row and at least one column held in place by a first electrical insulating member, a plurality of receiving cylinders arranged in a matching array of at least one row and at least one column and supported by a second electrical insulating member, such that on insertion of the plurality of dispense needles into the plurality of receiving cylinders a plurality of capacitors are formed. This embodiment of the sensor may be configured such that the needle tips of the dispense needles have to pass through at least one of said receiving cylinders in order to dispense a liquid into at least one of a plurality of wells arranged in a matching array so that each of the dispense needles corresponds to at least one of the plurality of receiving cylinders and at least one of the plurality of wells.

In addition this embodiment may further include a multiplexer and/or a demultiplexer. The multiplexer having a plurality of input channels and one output channel, wherein the plurality of receiving cylinders are connected to the plurality of input channels of the multiplexer, and the output channel is connected to an input of a voltmeter. The demultiplexer having one input provides channel and a plurality of output channels, wherein the input channel is connected to an output of a signal source and a plurality of dispense needles are connected to the said plurality of output channels of said demultiplexer.

A further embodiment provides a method of determining a volume of a dispensed liquid comprising introducing a target volume of a liquid sample into a dispense needle having a needle tip, dispensing an actual volume of the liquid sample from the dispense needle into a container, inserting the needle tip into a receiving cylinder thereby forming a capacitor, measuring the capacitance of the capacitor, and determining the presence of a lost volume of the dispensed liquid sample by comparing the measured capacitance value with a calibration capacitance value. A greater measured capacitance value when compared to the calibration capacitance value indicates the presence of a lost volume. The comparison of said measured capacitance value with a calibration capacitance value may be carried out by a processor.

BRIEF DESCRIPTION OF THE DRAWINGS

FIG. 23a refers to a homogeneous liquid layer in the overlap region, while FIG. 23b refers to the same amount of liquid (0.25 μL), but concentrated in the lower half of the overlap region.

DETAILED DESCRIPTION OF THE INVENTION

It has been found that, in needle-based dispensing systems, the target amount of liquid that is leaving the inner needle space is in many cases very well controlled, e.g., by the specific motion of a dispensing piston. The amount of liquid that is actually reaching the receiving well or other type of container may show discrepancies, however, because part of the liquid leaving the inner needle space is creeping along the outer diameter of the dispense needle and remains on the outer surface of the needle tip after the dispensing act has occurred. Therefore an amount of liquid is "lost" in the particular dispensing act. This mechanism may repeat itself in one or more successive dispensing acts and a substantial amount of liquid may accumulate, therefore, on the outer needle diameter. Once a critical amount of liquid has been accumulated, this liquid will "join" a dispensed droplet, generating an actual dispensed volume that by far exceeds the target dispense volume, which can result in significant inaccuracies in the results of subsequent assays.

This behavior is applicable to most types of liquids, for example the types of liquids and reagents utilized in the production of medical diagnostic assays such as microorganism identification (ID) and antimicrobial susceptibility determinations (AST), which may be a water based solution/suspension or a hydrocarbon based (e.g. ethanol) solution/suspension. A typical range of the target dispense volume is 0.5 μL to 100 μL. The type of container in which the liquid is dispensed into is typically a two-dimensional array of open wells, such as microtiter plates, however any small volume container is applicable.

Apparatus and methods for identifying and accurately quantifying volume loss during the dispensing of a liquid into a container are described below in accordance with the embodiments of the invention. The actual dispensed volume can then be used when calculating the subsequent assay results.

Figure 1:
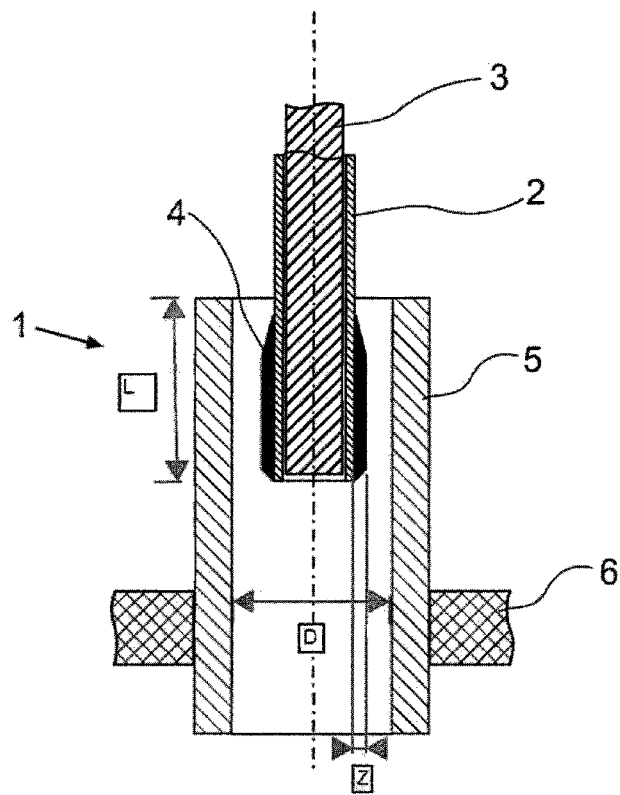
FIG. 1 is cross sectional view of a concentric cylinder capacitor arrangement in accordance with an embodiment of the subject invention, including a dispense loss volume along the outer diameter of the dispense needle.

An embodiment of a dispense volume sensor is illustrated in FIG. 1. The sensor, which in this case is a concentric cylinder capacitor arrangement 1, is formed by a dispense needle 2 and a receiving cylinder 5. In accordance with an embodiment of the invention, both needle 2 and cylinder 5 are made from electrically conducting materials, or from insulating materials with the needle's outer surface and the cylinder's inner surface being electrically conductive. Needle 2 is equipped with a movable inner piston 3 or some other mechanism to perform liquid sample aspiration and dispensing actions in various ways that are well-known in the art. Receiving cylinder 5 is mechanically supported and held in place by an electrically insulating member 6.

Figure 31:
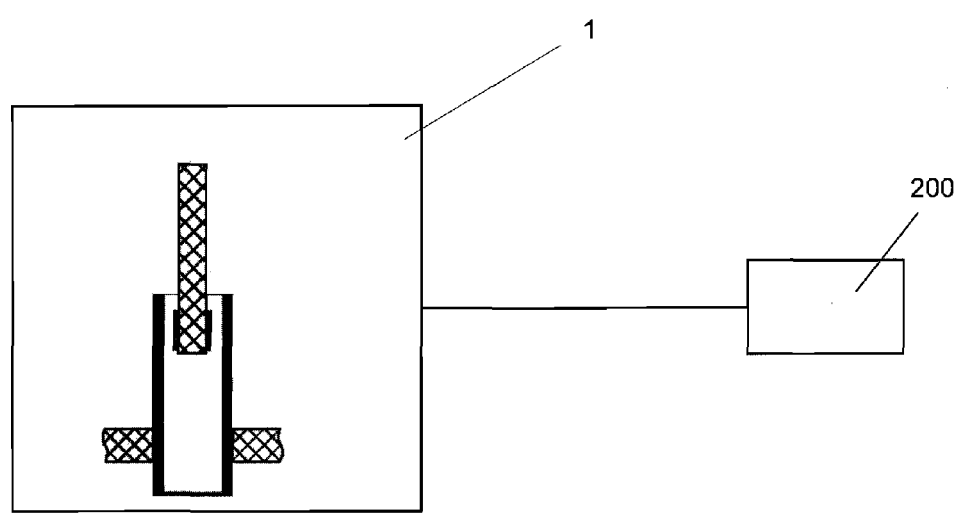
FIG. 31 illustrates a functional schematic depicting the cylinder capacitor arrangement of FIG. 1 in communication with a processor, in accordance with an embodiment of the invention.

In operation, in accordance with an embodiment of the invention, a needle 2 is first brought into contact with a liquid sample. Liquid is then aspirated into needle 2 by moving piston 3 upwards. The distance piston 3 is moved determines the volume of the aspirated liquid sample. As a precursor to performing a measurement according to an embodiment of the present invention, needle 2 is moved into cylinder 5 and held in a substantially concentric and coaxial position relative to cylinder 5, whereby needle 2 is inserted into cylinder 5 a certain distance L, forming an "overlap region", which represents the main contributor to the concentric cylinder capacitor. If, in the course of the aspiration step, or in the course of a dispensing step, some sample liquid 4 has remained on the outside of needle 2, the capacitance value of concentric cylinder capacitor arrangement 1 will be higher after the dispensing step, compared to the case where no liquid sample has remained on the outside of needle 2. Therefore, comparing the measured capacitance value after the dispensing step with a calibration capacitance value determined with no liquid on the outside of needle 2 allows one to determine if sample liquid 4 is present on the outside of needle 2. The comparison of the capacitance values can be completed by for example a processor or comparator 200. FIG. 31 illustrates a functional schematic depicting the cylinder capacitor arrangement of FIG. 1 in communication with a processor 200, in accordance with an embodiment of the invention.

Figure 32:
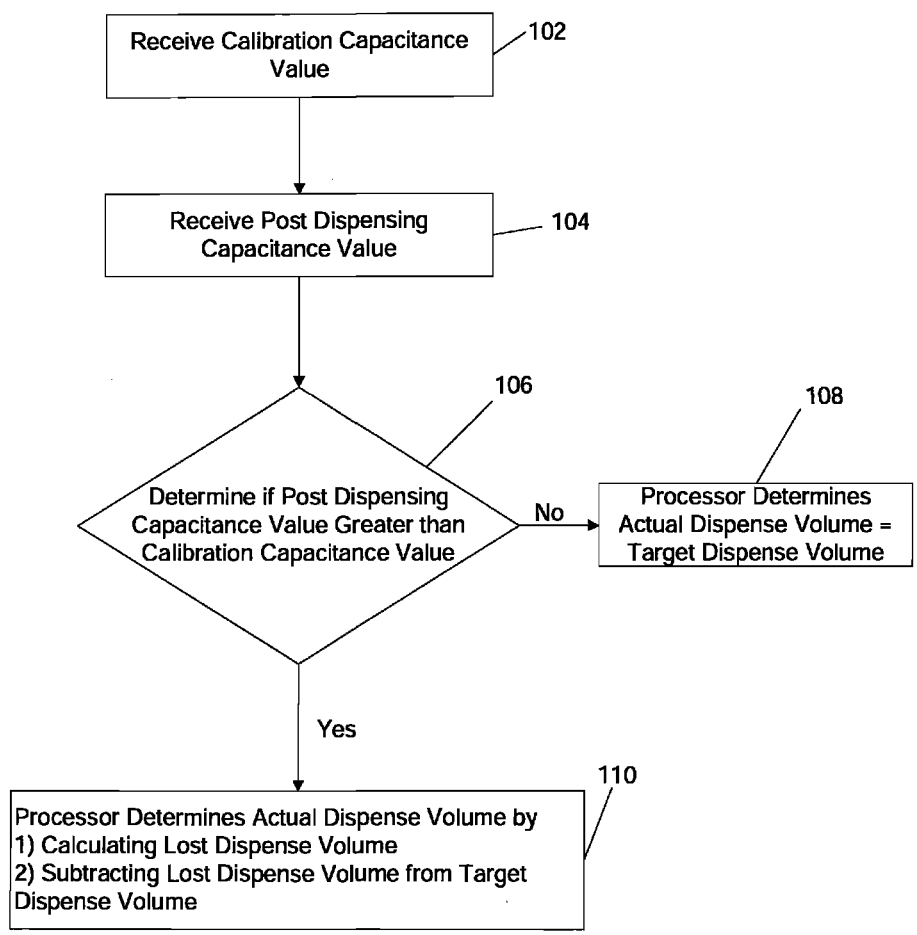
FIG. 32 illustrates a sequence of operation of a processor, in accordance with an embodiment of the invention.

FIG. 32 shows a sequence of operation of a processor 200 in accordance with an embodiment of the invention. The calibration capacitance value is received by the processor 200 (step 102). This predetermined valued would be accessed by processor 200 from memory or storage device (not shown). The post dispensing capacitance value is then received by the processor 200 from cylinder capacitor arrangement 1 (step 104) after the liquid has been dispensed. The processor 200 then determines if the post dispensing capacitance value is greater than the calibration capacitance value (step 106). If the post dispensing capacitance value is equal to the calibration capacitance value, the processor 200 then determines that the target dispense volume of liquid is equal to the actual dispensed volume of liquid and as such there is zero lost volume of dispensed liquid (step 108). However, if the post dispensing capacitance value is greater than the calibration capacitance value, the processor 200 then calculates the actual dispensed volume of liquid by, for example, subtracting the lost volume of dispensed liquid from the target dispense volume of liquid (step 110).

The actual dispensed volume and/or lost dispensed volume can then be used by the same processor 200 or by another processor in the calculation of the assay results. In addition the magnitude of the actual dispensed volume and/or lost dispensed volume may optionally be displayed on a visual display or the presence of a lost volume on the outside of a needle after the dispensing act indicated by a warning light.

In a dispense step, and in particular when using a "touch off" dispensing mode, in which the dispensed droplet is not ejected into the air space, but is brought into contact with the bottom of the receiving well, while still in contact with the dispense needle, the sample liquid 4 that is present at the outside of dispense needle 2 might join the intended dispense volume, causing an unintended dispensing error. By the way of example, suppose a target dispense volume of 5 μL has to be dispensed with 5% accuracy, then the volume of liquid 4 on the outside of needle 2 may not exceed an amount of 0.25 μL. Assuming a typical dispense needle diameter of 0.9 mm, and a length Y of liquid 4 of approximately 2 mm, a volume of 0.25 μL would result in a homogeneous liquid layer of thickness Z=42 μm (0.0016"). Such a layer of liquid can be detected reliably by a dispense volume sensor, according to an embodiment of the present invention. In fact a lost volume can be accurately detected for a target dispense volume as small 0.5 μL using a dispense volume sensor, according to an embodiment of the present invention.

Figure 2:
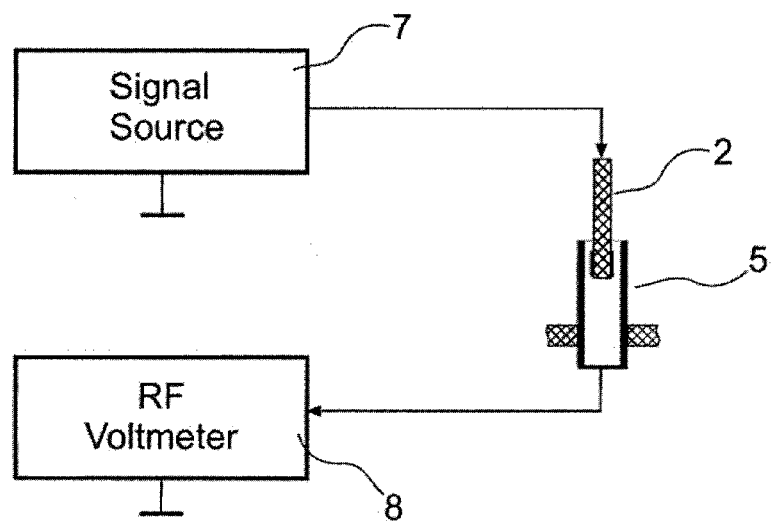
FIG. 2 shows a basic electrical configuration of a dispense volume loss sensor, according to an embodiment of the present invention.

FIG. 2 shows an electrical configuration for a dispense volume sensor, according to an embodiment of the present invention. A signal source 7 such as a sine-wave generator is connected to dispense needle 2, which forms one electrode of concentric cylinder capacitor arrangement 1 according to FIG. 1. Receiving cylinder 5, which forms the second electrode of concentric cylinder capacitor arrangement 1, is connected to an input of a RF voltmeter 8. It should be noted that a sensor according to the present invention is not restricted to the use of sinusoidal excitation, as other time-dependent periodic signals could also be used; however the following detailed description of the invention utilizes sinusoidal signals.

Figure 3:
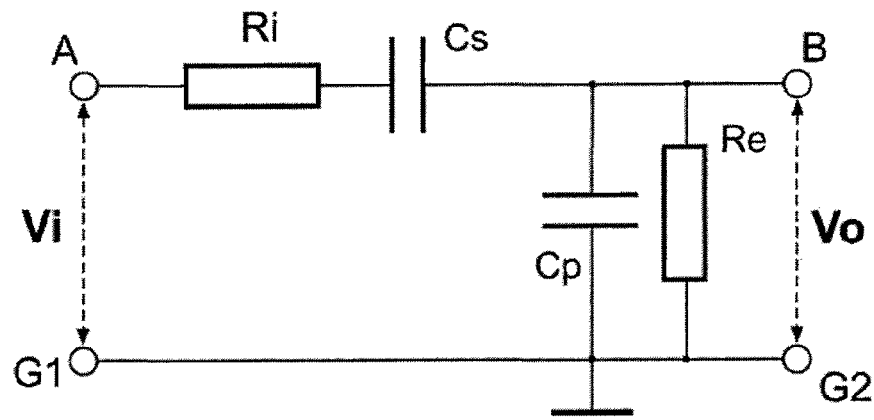
FIG. 3 depicts a circuit diagram for a dispense volume loss sensor, according to an embodiment of the present invention.
Figure 4:
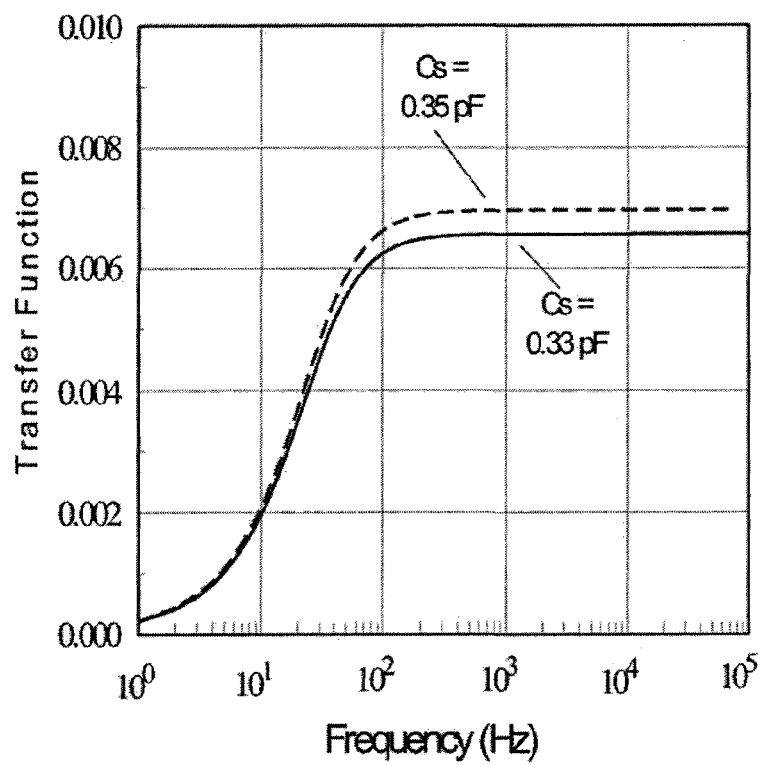
FIG. 4 shows a theoretical transfer function of the circuit diagram, according to FIG. 3, for capacitance values of 0.33 pF and 0.35 pF, respectively, assuming an input impedance of 100 MΩ for the RF voltmeter, according to an embodiment of the invention.

FIG. 3 shows the circuit diagram for a dispense volume sensor, according to an embodiment of the present invention, with a configuration as shown in FIG. 2. The sensor is receiving an input signal of voltage Vi from signal source 7 between nodes A and G1, respectively. Ri represents the output impedance of signal source 7 and has usually a relatively low value between 500Ω and 50Ω. Cs is the capacitance of concentric cylinder capacitor arrangement 1 and represents the "sensing capacitor". As is shown below, the value of Cs is typically well below 1 pF. Cp and Re represent the input capacitance and input impedance of RF voltmeter 8, including the capacitance of the cable connecting concentric cylinder capacitor arrangement 1 with RF voltmeter 8. The sensor setup is generating an output signal of voltage Vo between nodes B and G2, respectively. FIG. 4 shows the theoretical transfer function T(f)=Vo/Vi of the circuit diagram according to FIG. 3 for capacitance values of 0.33 pF and 0.35 pF for Cs, respectively, assuming an input impedance of 100 MΩ for the RF voltmeter and a value Cp=50 pF for the RF voltmeter plus the connecting cable. As can be seen from the plots in FIG. 4, Transfer function T(f) and, accordingly, the sensor output signal Voltage Vo become independent of frequency f, but dependent on the value of Cs. This means, no frequency stabilization is required when working at sufficiently high frequencies.

Figure 5:
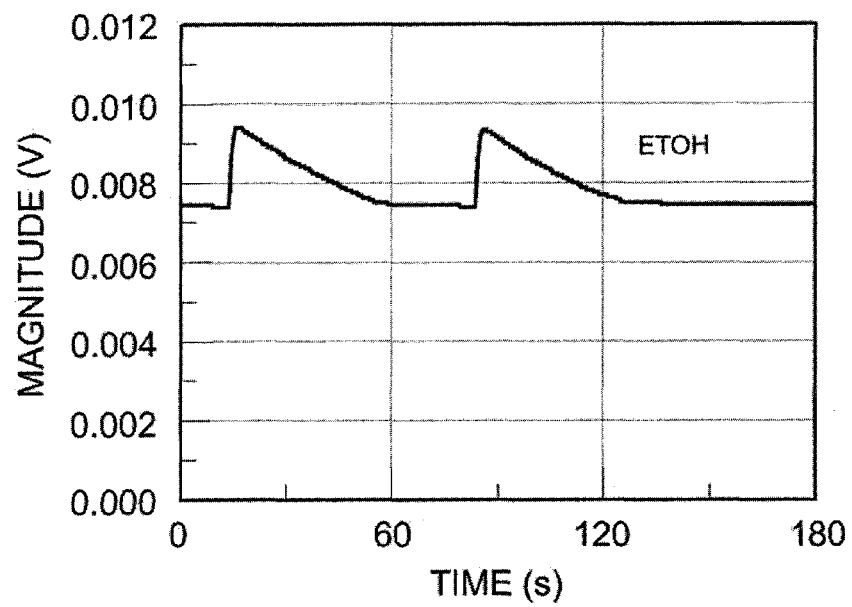
FIG. 5 shows a graph reflecting the deposition and subsequent evaporation of two individual 0.25-μL droplets of Ethanol onto the outer diameter of the dispense needle, according to an embodiment of the invention.

FIG. 5 shows a recording of voltage against time for dispense volume sensor, according to an embodiment of the present invention, reflecting the deposition and subsequent evaporation of two individual 0.25-μL droplets of ethanol (ETOH) onto the outer diameter of dispense needle 2 having an outer diameter of 0.9 mm in a concentric cylinder capacitor arrangement as shown in FIG. 1 including a receiving cylinder 5 with an inner diameter of 1.76 mm and an overlap region length L between needle 2 and cylinder 5 of 2 mm. Signal source 7 was operated at a frequency f=2 kHz and at a voltage Vi=1.5 V. RF voltmeter 8 had an input impedance Re=10 MΩ and an input capacitance Ce'=25 pF. The overall input capacitance was Cp=50 pF, considering the cable capacitance Cc=25 pF. The detection time constant was TC=300 ms. It should be noted that the step-like features in the recorded curve of FIG. 5 do not represent electronic noise, but the digitizing resolution. The RF voltmeter was operated in this experiment with a full-scale range of 2 V to protect the instrument in the event of a short circuit due to excessive amounts of liquid.

Figure 6:
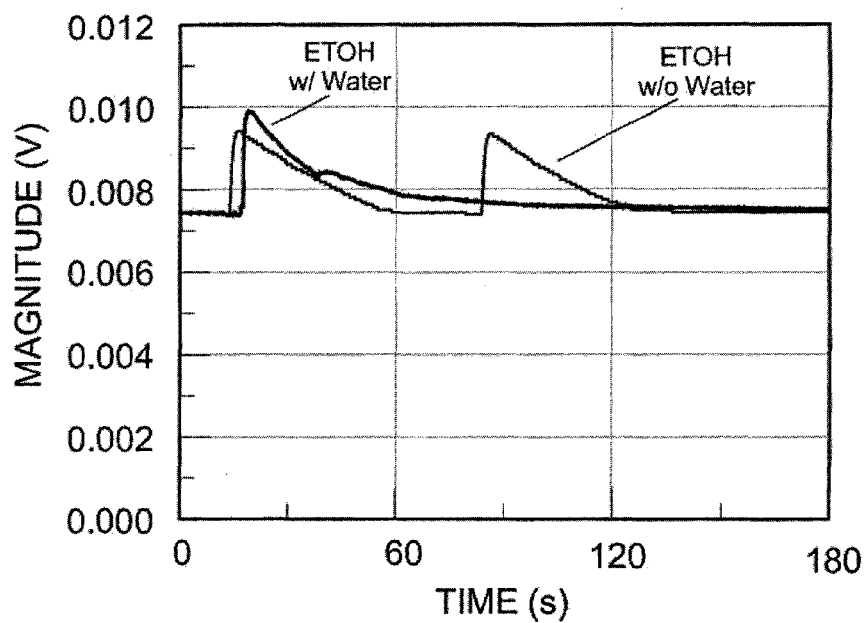
FIG. 6 corresponds to the graph in FIG. 5, and shows a graph reflecting the deposition and subsequent evaporation of two individual 0.25-μL droplets of Ethanol and water onto the outer diameter of the dispense needle, according to an embodiment of the invention.
Figure 7:
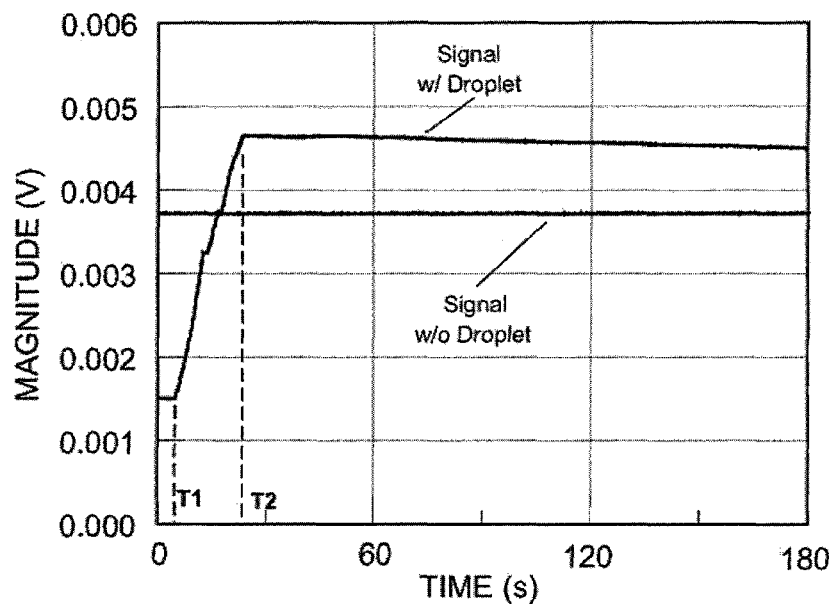
FIG. 7 shows a graph reflecting the output of a dispense volume sensor recording with and without a single 0.25-μL droplet of water onto the outer diameter of the dispense needle, in accordance with an embodiment of the invention.

FIG. 6 shows the reduction in evaporation rate on the incorporation of water into the ethanol droplets, when compared to the evaporation rate of ethanol without water. FIG. 7 shows a sensor recording of a single 0.25-μL droplet of water onto the outer diameter of the dispense needle 2. At time T1, the water droplet is disposed onto the outside of the needle tip. Between time T1 and T2, the needle 2 is coaxially inserted into the receiving cylinder 5 by 2 mm to create the overlap region. The sinusoidal excitation signal voltage has been reduced in this experiment from Vi=1.5 V to Vi'=0.75 V, which causes a reduction in the output signal voltage by 50%. The signal from the water droplet shows only a minor decrease over time due to the much lower evaporation speed. Considering the reduced excitation signal voltage, the droplet-related signal for water is almost identical to the corresponding signal for ethanol, despite of the fact that the dielectric constant of water, $\epsilon_W$=81, is significantly higher than the dielectric constant of ethanol, $\epsilon_{ETOH}$=24.6. This is an important advantage because, as the excitation signal voltage is independent of a material's dielectric constant, it allows for operating multiplexed sensor arrangements that handle a variety of different sample liquids.

Figure 8:
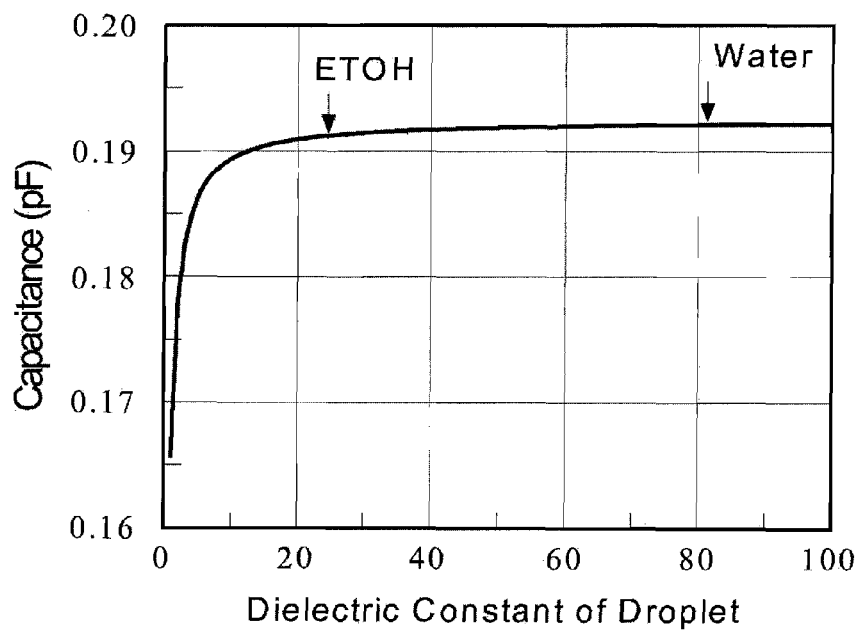
FIG. 8 shows a graph reflecting the capacitance value of a concentric cylinder capacitor according to the present invention as a function of the dielectric constant of a 0.25-μL droplet.

Thus, droplets of equal volume but with different dielectric constants typically generate dispense volume sensor signals that have similar signal voltages. FIG. 8 shows the capacitance value of a concentric cylinder capacitor according to an embodiment of the present invention as a function of the dielectric constant for a 0.25-μL droplet on the outside of the needle tip as calculated by MathCad software. This calculation is based on a needle with an outer diameter of 0.90 mm, a receiving cylinder with an inner diameter of 1.76 mm, and an overlap length L of 2 mm. The capacitance value for the empty cylinder which will be referred to as the calibration capacitance is 0.165 pF. As can be seen from FIG. 8, the capacitance value with a liquid droplet is relatively independent of the dielectric constant, which would allow handling a variety of liquids without re-calibration for each liquid. The behavior of the curve in FIG. 8 can be explained with the fact that the capacitance value of the "lost volume" liquid droplet portion of the concentric cylinder capacitor is much greater than the capacitance of the air space. Therefore, the overall capacitance value is dominated by the "air space" portion, which is independent of the dielectric constant of the liquid droplet.

Two variables which affect the magnitude and sensitivity of the sensor signal voltage for a given liquid droplet volume are the inner diameter D of the receiving cylinder 5 and the length of the overlap L between the dispense needle 2 and receiving cylinder 5 as shown in FIG. 1.

Figure 9:
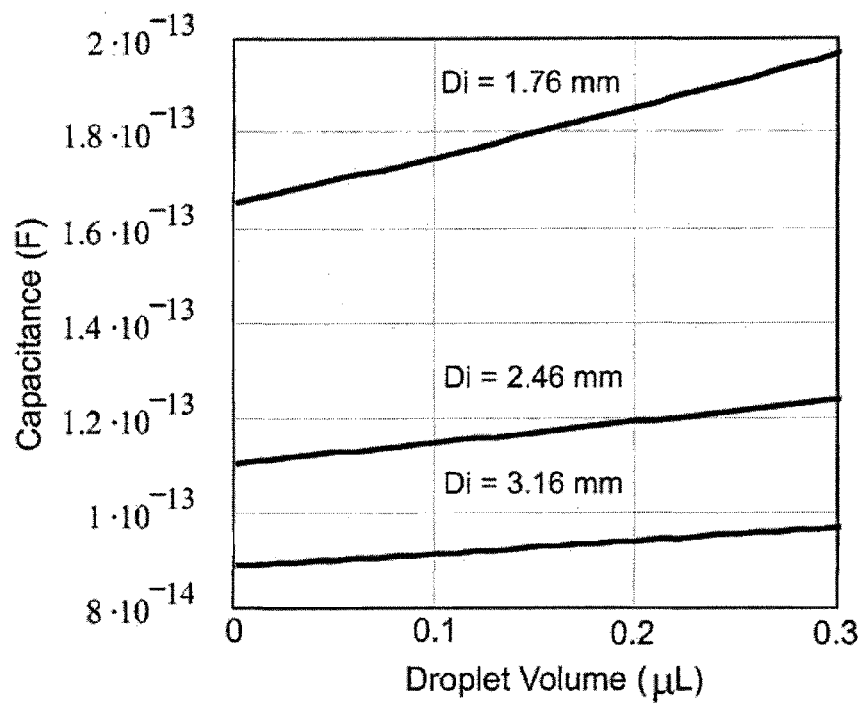
FIG. 9 shows a graph reflecting the impact of a varying inner diameter of the receiving cylinder on the change in capacitance for varying droplet volume, in accordance with an embodiment of the invention.

FIG. 9 shows the impact of a varying inner diameter of the receiving cylinder on the change in capacitance for a varying droplet volume. Receiving cylinders with inner diameters of 1.76 mm, 2.46 mm, and 3.16 mm, a dispense needle with an outer diameter of 0.90 mm, and an overlap length L of 2 mm have been assumed as calculated by MathCad software. The plots in FIG. 9 show that the detection sensitivity, i.e. the change in sensor signal voltage with increasing droplet volume, is decreasing with increasing inner diameter of the receiving cylinder. For an inner diameter of 1.76 mm, the sensor signal voltage is changing by 15.1% for a droplet of 0.25 μL volume. This change is reduced to 10.1% and 6.8% for inner diameters of 2.46 mm and 3.16 mm, respectively. While a smaller receiving cylinder will provide higher detection sensitivity, the danger of short circuits due to excess amounts of liquid will also increase.

Figure 10:
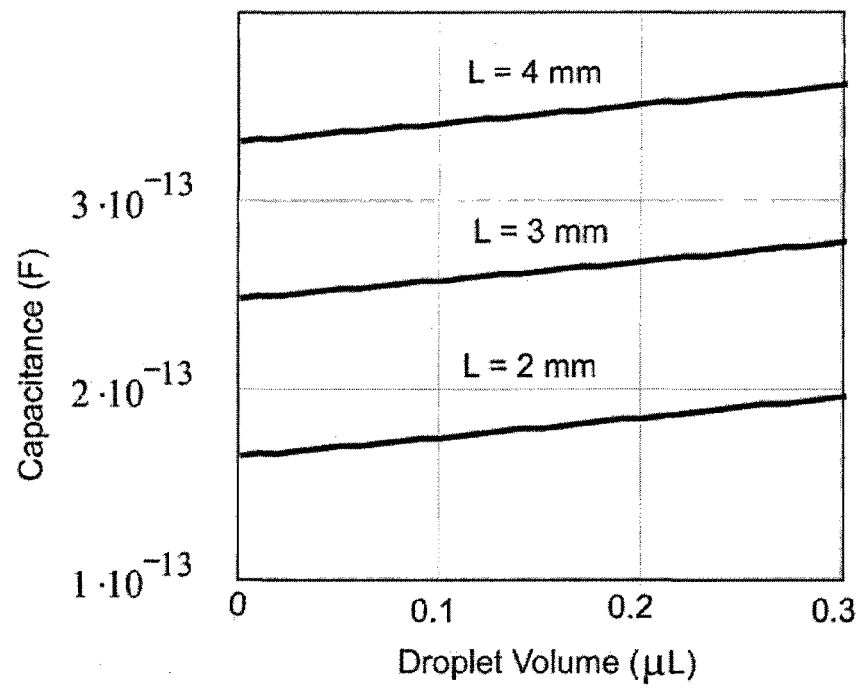
FIG. 10 shows a graph reflecting the impact of a varying overlap length of the dispense needle and receiving cylinder on the change in capacitance for varying droplet volume, in accordance with an embodiment of the invention.

FIG. 10 shows the impact of a varying overlap length of the dispense needle and receiving cylinder on the change in capacitance for varying droplet volume as calculated by MathCad software. Again, the calculation is based on a needle diameter of 0.9 mm and an inner diameter of 1.76 mm for the receiving cylinder. It has been assumed here that the liquid layer is extending over the whole overlap region length. For a 0.25-μL droplet, the sensor signal voltage is changing by 15.1%, 10.1%, and 7.6% for an overlap length of 2 mm, 3 mm, and 4 mm, respectively.

Figure 11:
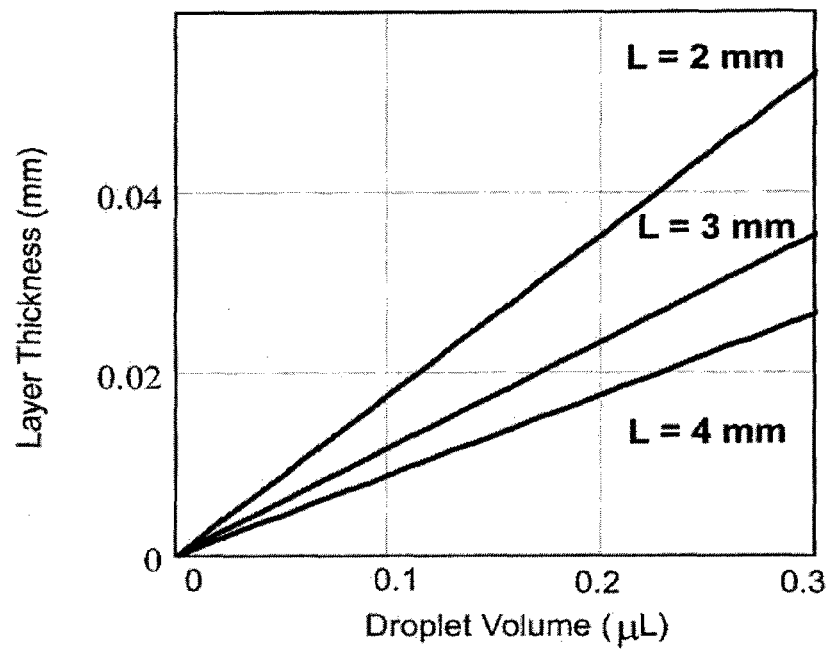
FIG. 11 shows a graph reflecting the estimated liquid layer thickness on the outside of the dispense needle as a function of droplet volume for varying overlap region length L of the dispense needle and receiving cylinder, in accordance with an embodiment of the invention.

While the plots in FIG. 10 indicate an advantage of a shorter overlap length L, "shorter droplets" mean thicker liquid layers Z. This is illustrated in the three plots in FIG. 11 for a dispense needle of 0.90 mm diameter that shows the estimated liquid layer thickness Z as a function of droplet volume for varying overlap length L of the dispense needle and receiving cylinder. It has been found in practicing the embodiment that an overlap length of 2 mm represents a good compromise.

It is important to provide a stable baseline voltage for a dispense volume sensor according to an embodiment of the present invention, in order to provide a consistent and stable calibration capacitance value determined with no liquid on the outside of needle 2. Two factors which affect the baseline voltage of the sensor signal voltage are the radial and longitudinal positions of the dispense needle relative to the receiving cylinder.

Figure 12:
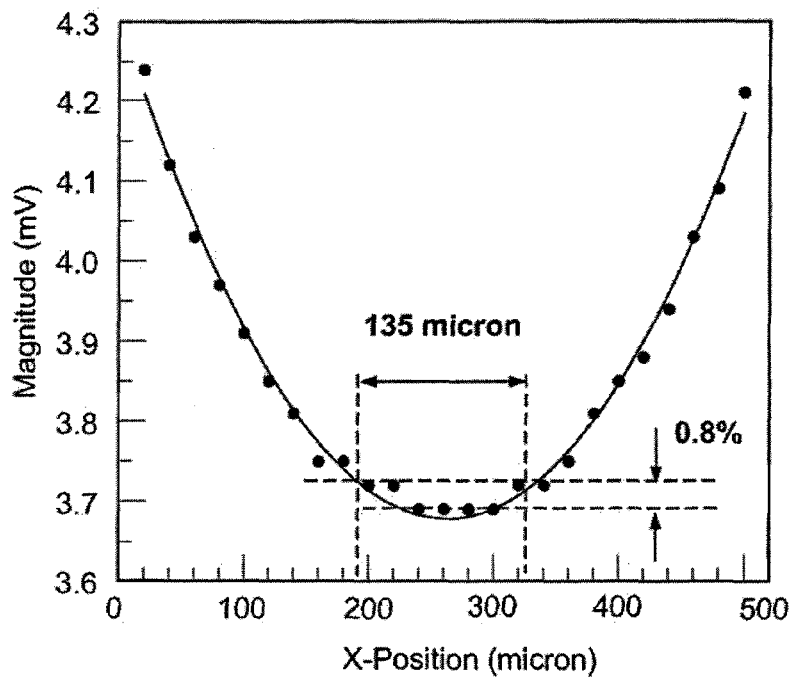
FIG. 12 shows a graph reflecting the measured sensor baseline output signal as a function of the dispense needle radial position along the inner diameter of the receiving cylinder, in accordance with an embodiment of the invention.

FIG. 12 depicts the measured dispense volume sensor baseline output signal voltage as a function of the dispense needle's radial position along the inner diameter of the receiving cylinder. The dispense needle had a diameter of 0.90 mm, and the receiving cylinder had an inner diameter of 1.76 mm. The plot shown in FIG. 12 provides an estimate for the required radial positioning accuracy of the dispense needle along the inner diameter about the center of the receiving cylinder. This plot shows that the dispense needle's radial position may vary within a range of 135 μm along the inner diameter, about the center of the receiving cylinder diameter, in order to achieve a base line voltage variation of less than 1%. It should be noted that a droplet of 0.25 μL volume will cause a 25% increase in the signal voltage when compared to the base line voltage, so that droplet detection is clearly and reliably indicated.

Figure 13:
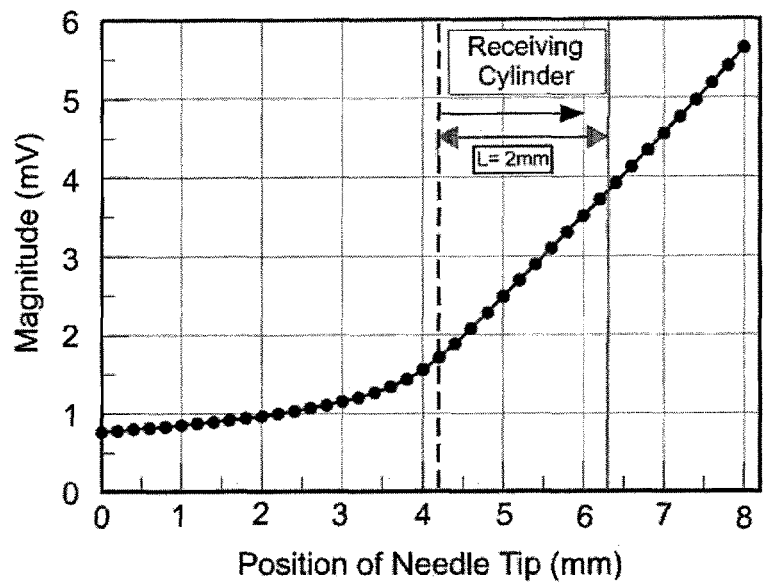
FIG. 13 shows a graph reflecting a measurement of the sensor baseline output signal versus the vertical position of the needle tip relative to the outer cylinder, in accordance with an embodiment of the invention.

The base line voltage is also dependent on the longitudinal position of the dispense needle tip inside the receiving cylinder i.e. the overlap length L. FIG. 13 shows a measurement of the dispense volume sensor baseline output signal versus the longitudinal position along the Y-axis of the needle tip relative to the receiving cylinder. The recordings shown in FIGS. 7, 14, 15, and 16 have been performed with the position of the needle tip according to FIG. 13 at position 6.2 mm, which corresponds to an overlap length L of 2 mm and results in a base line voltage of 3.75 mV. The plot in FIG. 13 shows a change in base line voltage per change in needle tip position of 1.05 mV/mm inside the receiving cylinder. This means that the longitudinal position of the needle tip inside the receiving cylinder should, at least for the parameters of this experiment, be controlled with a precision of 36 μm to guarantee a base line stability of 1% for the 3.75-mV base line voltage.

Figure 17:
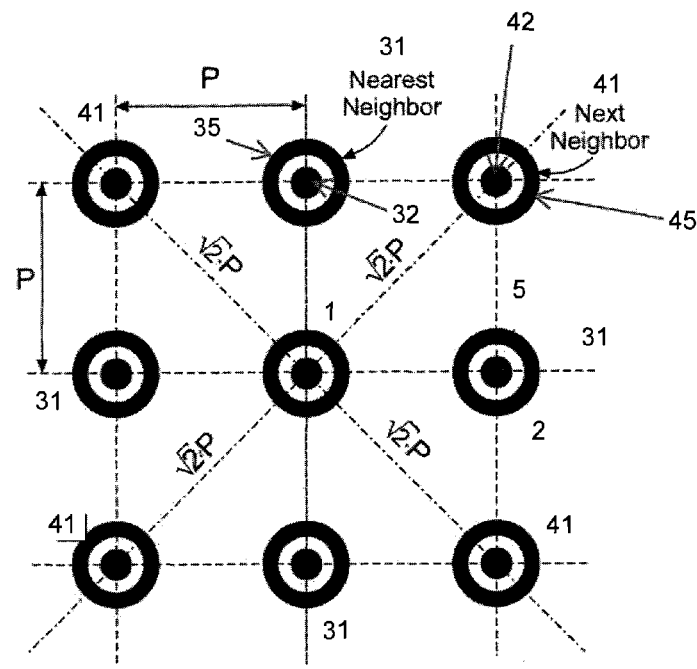
FIG. 17 shows a two-dimensional array of electrically active dispense needles, in accordance with an embodiment of the invention.

A dispense volume sensor according to one embodiment of the present invention may be used in a multiplexed version comprising an array of at least one row and at least one column of dispense needles, e.g., whereby the dimensions of this array match the dimensions of a multi-well plastic plate. FIG. 17 depicts such an array with a concentric cylinder capacitor 1 in the center comprising a dispensing needle 2 and receiving cylinder 5, and all its surrounding neighboring capacitors 31 and 41 having a pitch of P=5.81 mm. In such situation, more than one or even all the dispense needles 2, 32, and 42 could be activated with a sinusoidal RF voltage simultaneously. This means that any given receiving cylinder 5 might receive additional RF field contributions from "Nearest Neighbor" needles 32 and from "Next Neighbor" needles 42. Each activated neighboring needle can only induce a voltage on the central receiving cylinder 5 with those parts of the neighboring needle that protrude above the top of their respective neighboring cylinders 35 and 45. Thus, the experiment illustrated in FIG. 18 was performed with the activated needle tip at equal height with the top of its own receiving cylinder 5 i.e. the overlap length L=0, in order to maximize the additional RF field contributions.

Figure 18:
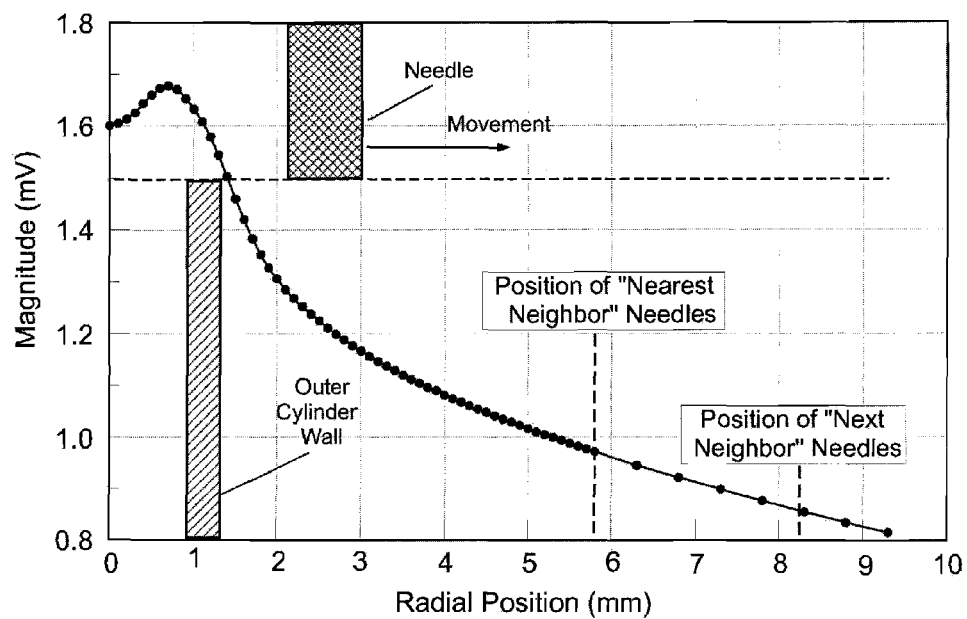
FIG. 18 shows a graph reflecting a measurement of the sensor baseline output signal versus the radial position of the dispense needle, in accordance with an embodiment of the invention.

FIG. 18 shows a graph reflecting in accordance with an embodiment of the invention measurement of the dispense volume sensor baseline output signal versus the radial position of the dispense needle 2. Here, an activated needle 2 was moved from the usual central position, which is the radial position "0" in FIG. 18, in radial direction towards positions where nearest 32 and next 42 neighbors would be located within an array having a pitch of P=5.81 mm. In essence, the plot in FIG. 18 shows that needles positioned at next 32 and nearest 42 neighbor positions may still induce a sensor signal in the receiving cylinder shown at the left side of the graph. It is expected, however, that a possible thin liquid droplet layer on such neighboring needles 32 and 42 would have no impact on the induced voltage. In other words, it is believed that next and nearest neighbors will have a fixed impact on the sensor base line, but will not contribute to the sensor output signal.

Figure 19:
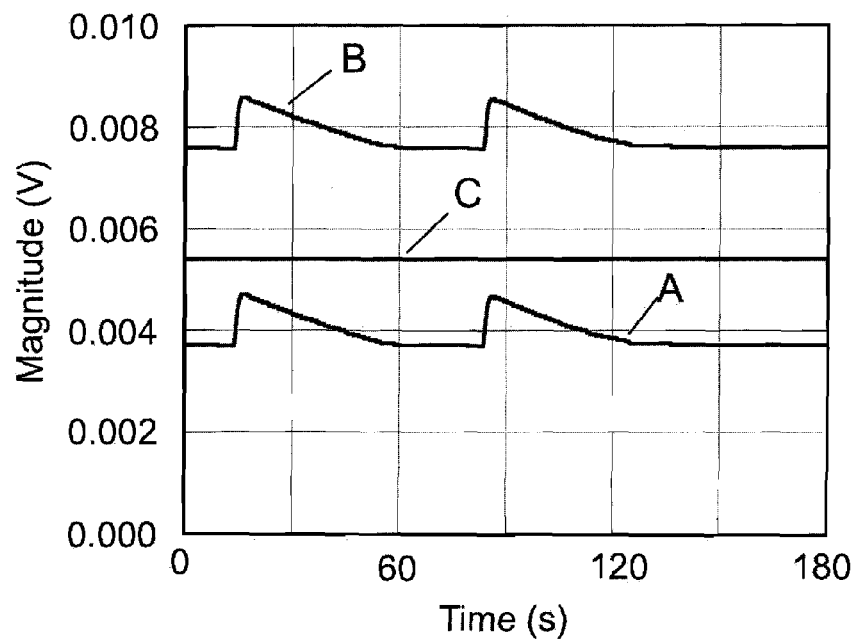
FIG. 19 shows a graph reflecting the estimated additional baseline contribution from next neighbors of a dispense needle, in accordance with an embodiment of the invention.

FIG. 19 shows a graph reflecting the estimated additional baseline contribution from next neighbors 32 of a dispense needle 2, in accordance with an embodiment of the invention. Curve A shows a dispense volume sensor recording of two 0.25-μL droplets of ethanol with only one dispense needle 2 activated. Curve B shows the signal with the calculated additional baseline contribution from the four next neighbor dispense needles 32 as shown in FIG. 17, based on the measurement illustrated in FIG. 18. Curve C in FIG. 19 shows the actual measured base line with the four nearest neighbor dispense needles 42 activated. As can be seen, the measured base line contribution is well below the estimated contribution.

Figure 20:
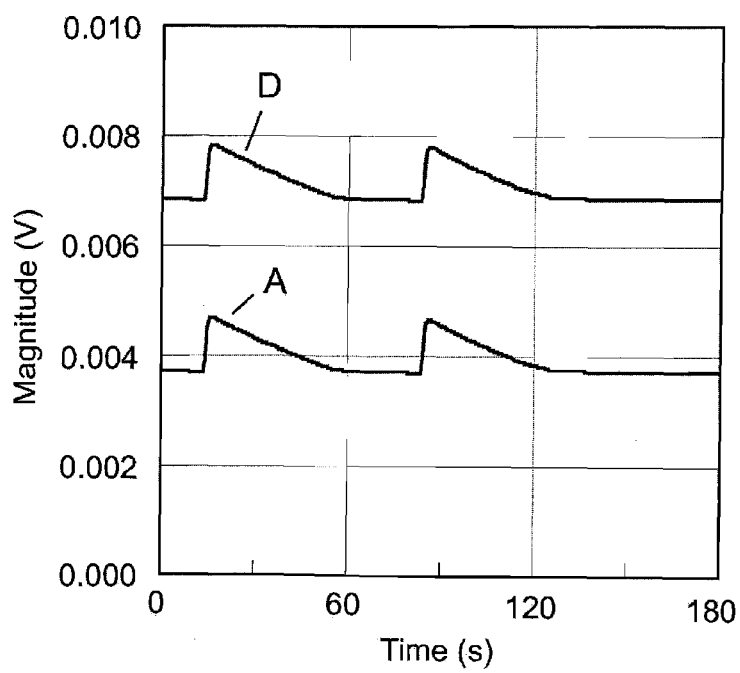
FIG. 20 shows a graph reflecting the estimated additional baseline contribution from next and nearest neighbors of a dispense needle, taking into account the result of a measurement with four neighbors, in accordance with an embodiment of the invention.

FIG. 20 shows a graph reflecting the estimated additional baseline contribution from next 32 and nearest 42 neighbors of a dispense needle 2, taking into account the result of a measurement with four neighbors, in accordance with an embodiment of the invention. Curve A is again a dispense volume sensor recording of two 0.25-μL droplets of ethanol with only one dispense needle activated, and curve D is depicts a newly estimated signal with eight nearest and next neighbor dispense needles activated, based on the four-neighbor result of FIG. 19, curve C. The conclusion, which can be drawn from FIG. 20, is that droplets of 0.25 μL volume can be easily detected, even within an array of simultaneously activated neighbor needles.

Figure 21:
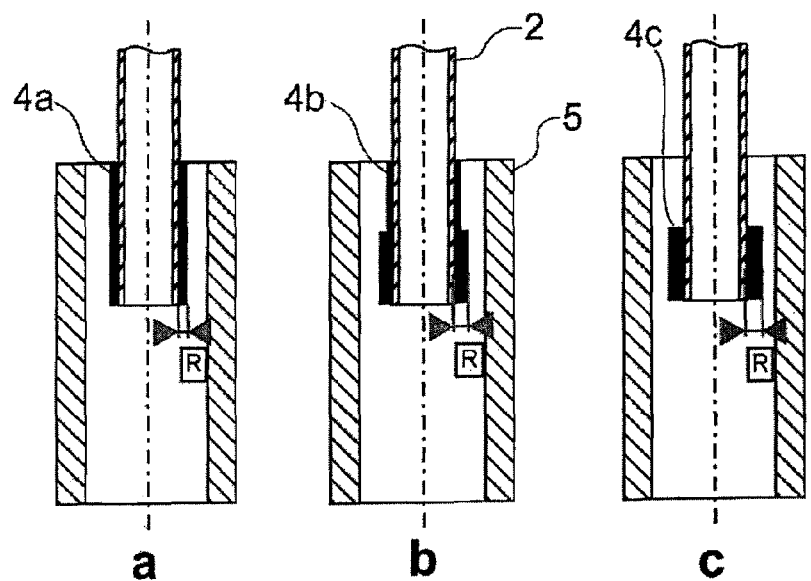
FIG. 21 shows a graph reflecting simplified possible profile shapes for a 0.25-μL droplet on the outer diameter of a dispense needle, in accordance with an embodiment of the invention.
Figure 22:
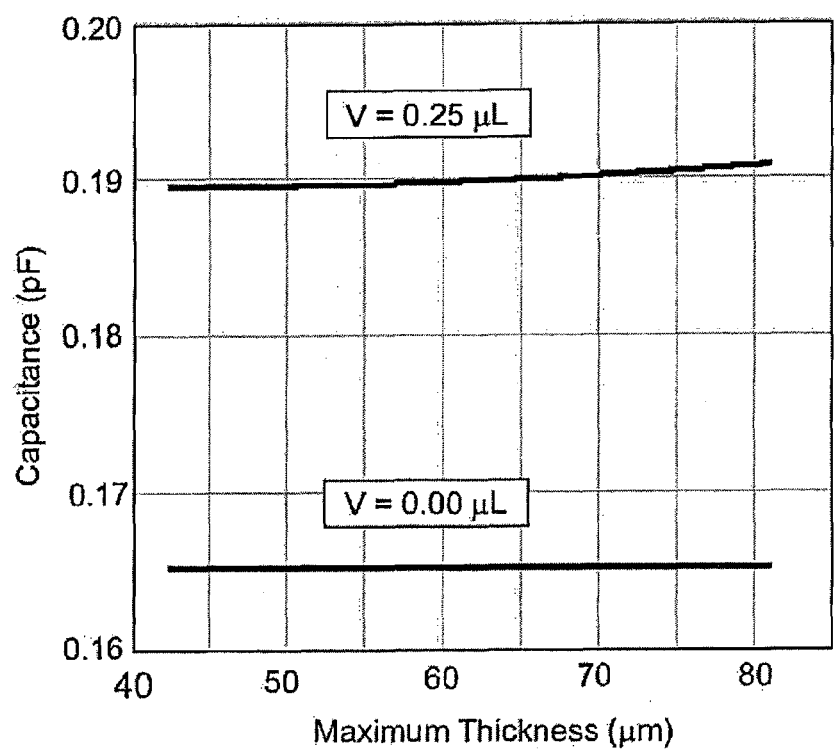
FIG. 22 a graph illustrating the impact of changes in the droplet profile on the capacitance value, in accordance with an embodiment of the invention.

So far it has been assumed that the droplets of the lost dispense volume 4 are distributed as a layer of constant thickness along the outside of dispense needle 2 over the full overlap region. FIG. 21 shows simplified possible profiles a, b, & c for a droplet of constant volume, in order to estimate the impact of changes in the droplet's shape. FIG. 22 illustrates the impact of changes in the profile of a 0.25-μL droplet according to FIG. 21 on the expected capacitance value with capacitance plotted against the maximum thickness of the droplet R, which is defined as the thickness within the lower half of the overlap region.

In FIG. 21a, the droplet 4a has a constant thickness along the entire overlap region which corresponds to R=42 μm. In FIG. 21c, no liquid is remaining in the upper half of the overlap region, and the droplet 4c has a constant thickness within the lower half of the overlap region which results in R=81 μm. In FIG. 21b, the layer thickness of droplet 4b is greater in the lower half of the overlap region so that R will be equal to a value within the range of 42 μm to 81 μm. The upper curve in FIG. 22 shows the how the capacitance changes if the maximum thickness R, hence droplet profile is increased from thickness to another. As can be seen, there is only a minor impact, and a dispense volume sensor according to the present invention responds to a variety of droplet profiles. The lower curve in FIG. 22 represents the calibration capacitance, which corresponds to a droplet volume of 0 μL.

Figure 23:
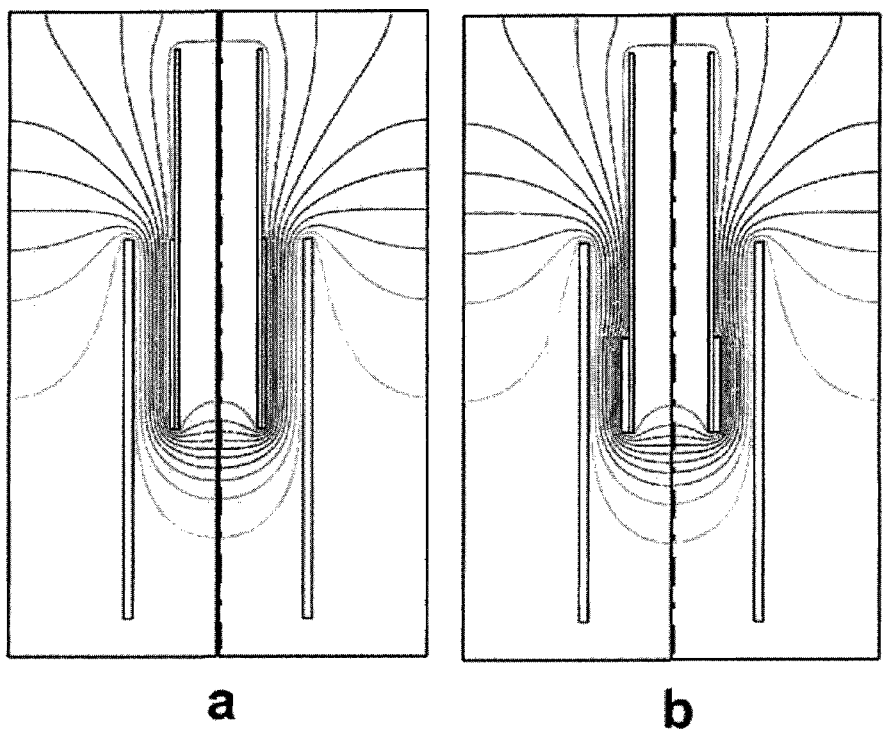
FIG. 23 are contour plots for the complete electric field distribution near the concentric cylinder capacitor, according to the present invention, as calculated using a COMSOL Multiphysics-3.3 program.

In the preceding paragraphs, the capacitance values for the concentric cylinder capacitor arrangements were calculated using MathCad software without considering stray fields. Stray fields are fields that occur beyond the internal overlap region between dispense needle 2 and receiving cylinder 5. Therefore the corresponding capacitance values were recalculated, to include the stray fields, by using the COMSOL Multiphysics software program. In this case, the dispense needle has an outer diameter of 0.90 mm, the receiving cylinder has an inner diameter D of 1.76 mm, and the overlap region length L is 2 mm. FIGS. 23a and 23b depict contour plots for the complete electric field distribution near the concentric cylinder capacitor according to the present invention, as calculated using the COMSOL Multiphysics-3.3 program. FIG. 23a refers to a homogeneous liquid layer of constant thickness in the overlap region as shown in FIG. 21a, while FIG. 23b refers to the same amount of liquid (0.25 μL), but concentrated in the lower half of the overlap region, as shown in FIG. 21c. While, the contour plots in FIGS. 23a and 23b clearly show that the electric field is extending far beyond the overlap region into the outer space, it appears that the droplet profile only has an impact on the field distribution near the droplet inside the overlap region, but almost no impact on the field distribution farther away from the droplet. This observation leads to the conclusion that taking the stray field components into account may result in a higher base line capacitance, but does not have a great influence on the droplet-related sensor signal changes.

The following Table 1 demonstrates this:

TABLE 1

| Volume (µL) | C1 $(10^{-13}\,F)_{MathCad}$ | C2 $(10^{-13}\,F)_{COMSOL}$ | C2 − C1 $(10^{-13}\,F)$ |
| --- | --- | --- | --- |
| 0 | 1.653 | 2.536 | 0.88 |
| 0.25 | 1.896 | 2.810 | 0.91 |

The capacity values C1 in Table 1 were calculated using MathCad software, and no stray field components have been taken into account. The capacity values C2 in Table 1 were calculated using COMSOL Multiphysics software, in which stray field components have been taken into account. The numbers in this table show that considering stray field components results in a capacitance that is consistently higher by approximately $0.90*10^{-13}$ F, regardless of the presence of a 0.25-µL liquid droplet within the concentric cylinder capacitor. Thus, the stray field components are adding a constant term to the base line capacitance value.

Figure 14:
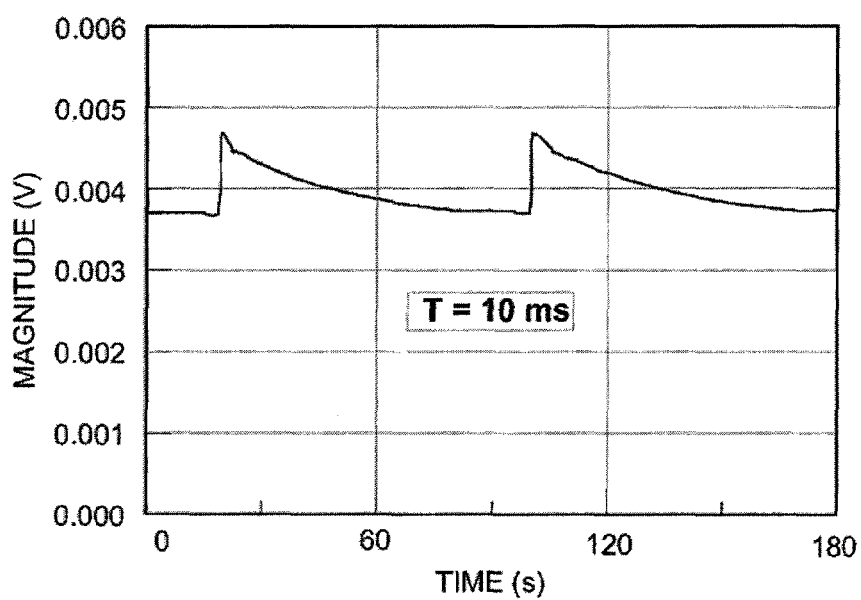
FIG. 14 shows a graph reflecting a dispense volume sensor for two individual 0.25-μL droplets of Ethanol, applying a detection time constant of 10 ms, in accordance with an embodiment of the invention.
Figure 15:
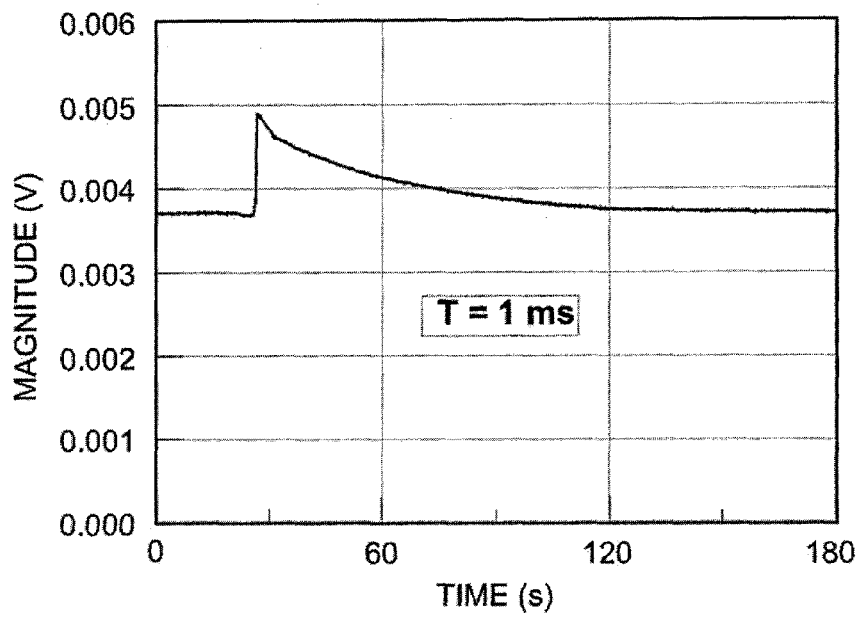
FIG. 15 shows a graph reflecting a dispense volume sensor recording for a single 0.25-μL droplet of Ethanol, applying a detection time constant of 1 ms, in accordance with an embodiment of the invention.
Figure 16:
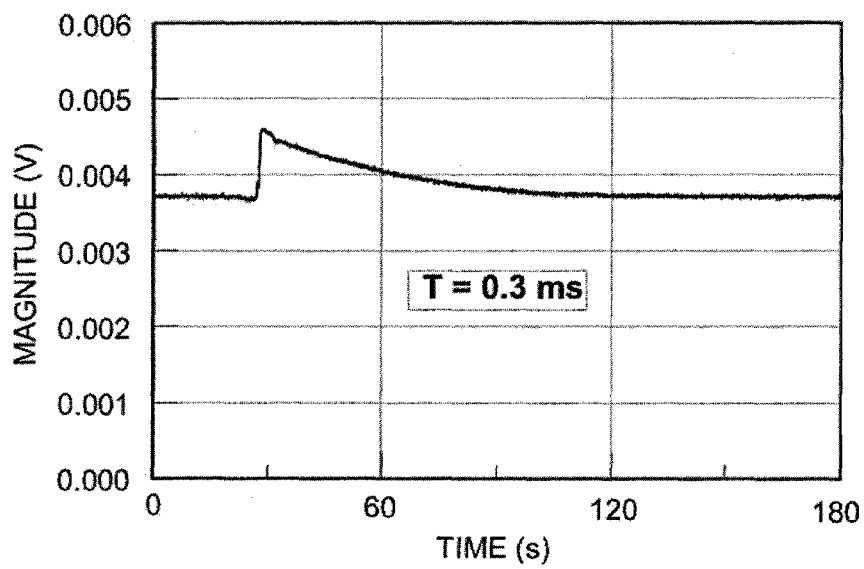
FIG. 16 shows a graph reflecting a dispense volume sensor recording for a single 0.25-μL droplet of Ethanol, applying a detection time constant of 0.3 ms, in accordance with an embodiment of the invention.

To operate a multiplexed dispense volume sensor according to an embodiment of the present invention it is typically desirable that the time needed for executing a measurement be small. FIGS. 14, 15, and 16 show dispense volume sensor recordings of a single 0.25-µL droplet of ethanol with detection time constants of 10 ms, 1 ms, and 0.3 ms, respectively.

As described below, a suitable signal-to-noise ratio is obtained even in the case of 0.3 ms.

Figure 24:
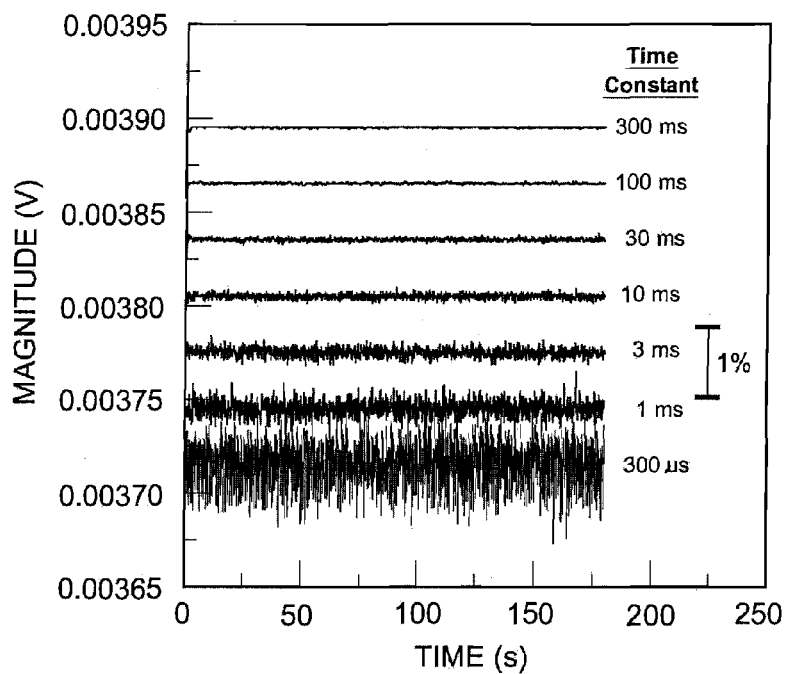
FIG. 24 a graph depicting noise recordings in the dispense volume sensor output signal for varying detection time constants between 300 ms and 300 μs, in accordance with an embodiment of the invention.

FIG. 24 shows noise recordings in the dispense volume sensor output signal for varying detection time constants between 300 ms and 300 µs in more detail. The individual plots were shifted by 0.03 mV for clarity. For a detection time constant of 0.3 ms, the peak-to-peak noise voltage amounts only to about 1% of the sensor output signal voltage. In other words, a 0.25-µL droplet of liquid can be detected with a signal-to-noise ratio of 100:1. This means that a dispense volume sensor 1 according to embodiments of the present invention may be suitable to scan 150 individual dispense needles for the presence of liquid in less than one second.

Figure 25:
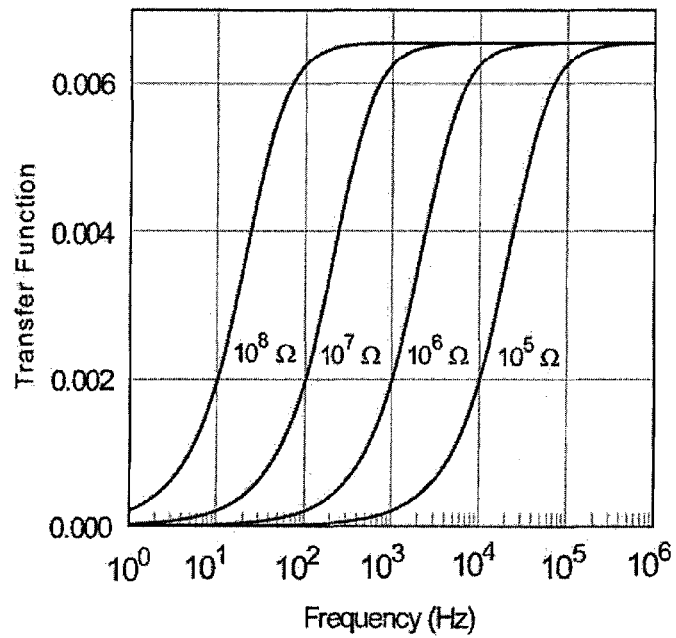
FIG. 25 shows a graph reflecting the theoretical transfer function of the circuit diagram according to FIG. 3 for a capacitance value of 0.33 pF, assuming input impedance values Re between of 0.1 MΩ and 100 MΩ for the RF voltmeter, in accordance with an embodiment of the invention.

The transfer function as depicted in FIG. 4 refers to an RF voltmeter with an input impedance value Re=100 MΩ. Thus, a lower input impedance value may be also required in order to achieve a short data acquisition time for a multiplexed dispense volume sensor. FIG. 25 shows the theoretical transfer function of the circuit diagram according to FIG. 3 for a capacitance value of 0.33 pF, assuming input impedance values Re between of 0.1 MΩ and 100 MΩ for the RF voltmeter. As can be seen, the same plateau value can be achieved for all impedance values by adjusting the operating frequency accordingly.

Figure 26:
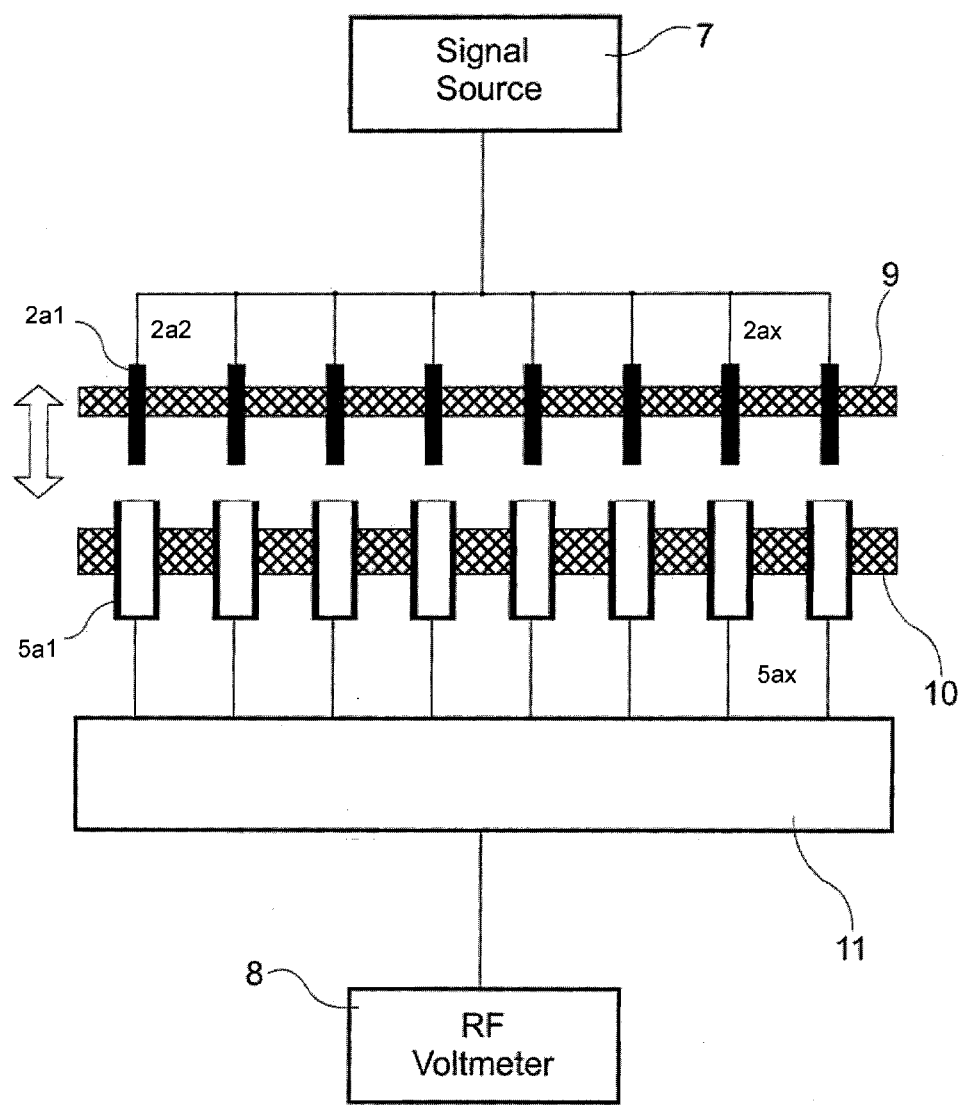
FIG. 26 shows a dispense volume sensor, comprising a multiplexed concentric cylinder capacitor arrangement, in accordance with an embodiment of the invention.

FIG. 26 shows a dispense volume sensor according to an embodiment of the present invention, comprising a multiplexed concentric cylinder capacitor arrangement. A multiplexer or mux (occasionally the term muldex is also found, for a combination multiplexer-demultiplexer) is a device that performs multiplexing; it selects one of many analog or digital input signals and outputs that signal into a single line. A signal source 7 is connected in parallel with all dispense needles $2a_x$ of the array (where x is equal to the total number of needles in the array). Needles $2a_x$ are mechanically supported and held in place by an electrically insulating member 9. Receiving cylinders $5a_x$ (where x is equal to the total number of cylinders in the array) are arranged in a matching array and supported by an electrically insulating member 10. All receiving cylinders $5a_x$ are connected with the inputs of a multiplexer 11. The output of multiplexer 11 is finally connected with the input of an RF voltmeter 8. A multiplexer therefore can be considered as a multiple-input, single-output switch, and a demultiplexer as a single-input, multiple-output switch. A measurement is performed after the dispense step, on all the needles $2a_x$ in the array, member 9 is positioned towards receiving cylinders $5a_x$ until an appropriate overlap length between needles $2a_x$ and receiving cylinders $5a_x$ is achieved. A common computer (not shown) is used to control multiplexer 11 in such a way that all the needles $2a_x$ in the array are being scanned in a serial mode of operation. The recorded signals are then compared with a set of base line signals that were recorded earlier with no liquid droplets present on needles $2a_x$. If none of the recorded signals exceeds the corresponding base line signal, no droplets are present.

Figure 27:
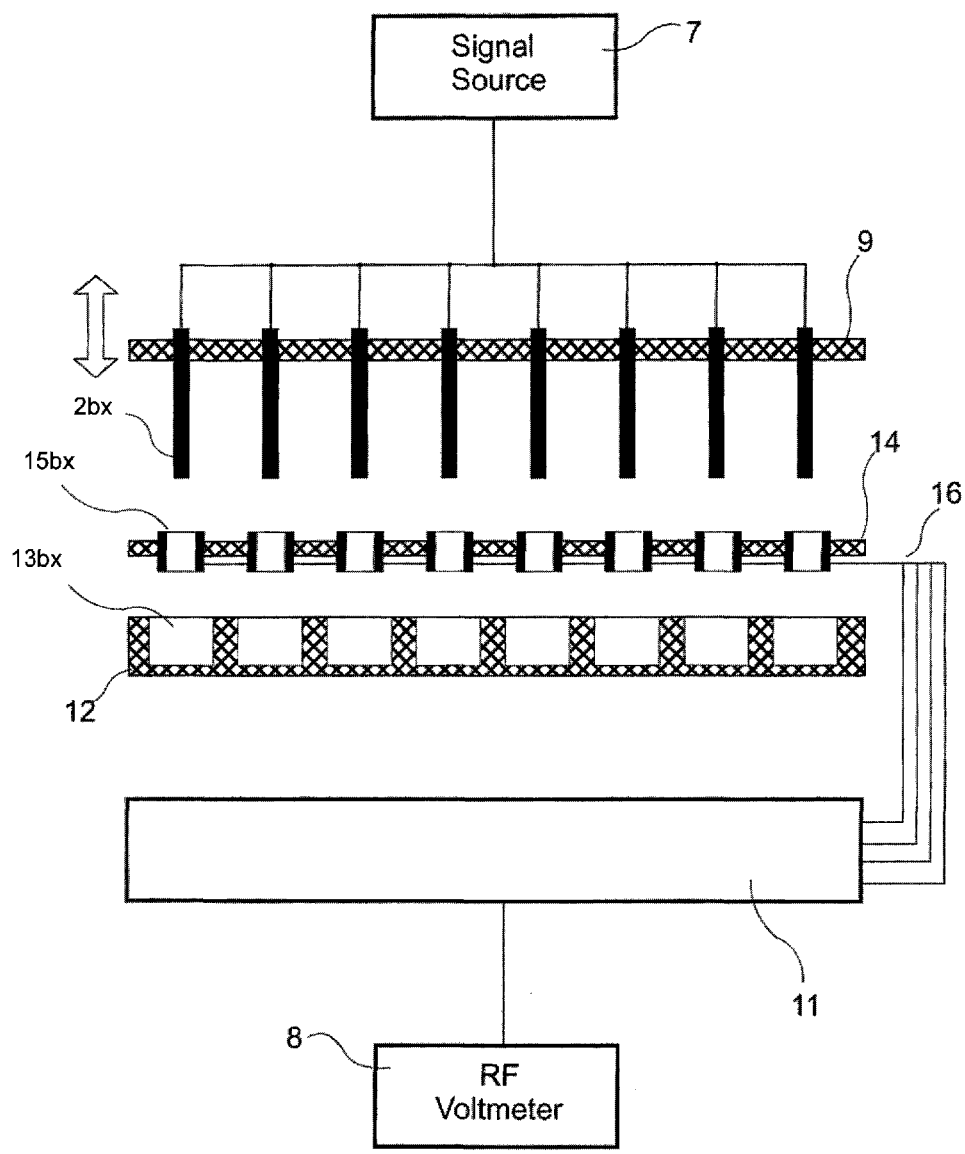
FIG. 27 shows a dispense volume sensor, wherein the array of dispense needles is passing through the matching array of cylinders, while moving towards and away from the array of wells, respectively, in accordance with an embodiment of the invention.

FIG. 27 shows yet another embodiment of a dispense volume sensor according to the present invention, wherein the array of dispense needles $2b_x$ is passes through a matching array of receiving cylinders $15b_x$, while moving towards and moving away from the array 12 of wells $13b_x$, respectively (where x is equal to the total number of needles/cylinders/wells in the array). The array of receiving cylinders $15b_x$ are supported and held in place by a member 14. In the sensor arrangement of FIG. 27, receiving cylinders 15 are insulated from each other and connected with the inputs of multiplexer 11 through wire harness 16. The sensor arrangement depicted in FIG. 27 has a number of advantages. First, the array of dispense needles $2b_x$ does not have to make a detour on its way towards the array of wells $13b_x$, in order to take a capacitance measurement, which saves time. Second, the array of dispense needles $2b_x$ may be checked for the presence of reservoir liquid, prior to the dispense step. Third, the array of dispense needles $2b_x$ can be re-checked, this time for dispense volume on its travel away from the array of wells $13b_x$, after executing the dispense step.

Figure 28:
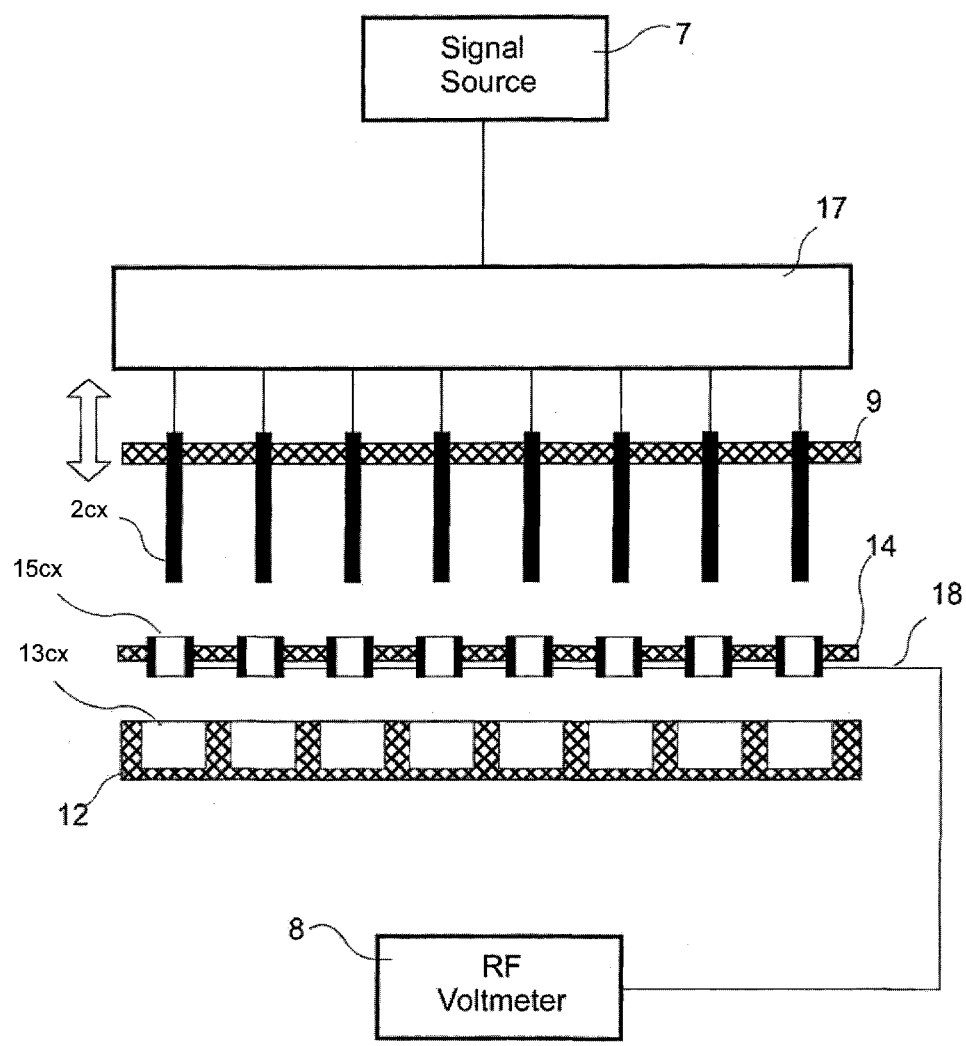
FIG. 28 shows an embodiment of the dispense volume sensor, similar to the arrangement shown in FIG. 27, but with the dispense needles electrically activated in a series mode, and the receiving cylinders connected in parallel with the RF voltmeter.

FIG. 28 shows a further embodiment of a dispense volume sensor according to the present invention, which is similar to the arrangement shown in FIG. 27, but with the dispense needles electrically activated in a series mode by computer-controlled (computer not shown) demultiplexer 17. All receiving cylinders $15c_x$ are connected with each other, and connected with the input of RF voltmeter 8 via cable 18. The additional advantage of this setup over the setup shown in FIG. 27 is the fact that demultiplexer 17 can have extremely low output impedance values of 50Ω or even less, which allows for extremely fast operation, and without ending up with an extremely small transfer function. In the setup of FIG. 28, only one dispense needle 2 would be electrically active at any given time, and only one cylinder 15 would "receive" an RF electric field. All other cylinders would face an in-active needle at constant electrical ground potential. Therefore, all other cylinders would act as one capacitor Cp' in parallel to capacitor Cp in the circuit diagram shown in FIG. 3. If, e.g., the array has 136 needles of 0.90 mm diameter and 136 receiving cylinders of 1.76 mm inner diameter, and if the overlap length is 2 mm, then the 135 "other" concentric cylinder capacitors would, according to Table 1, represent a capacitor Cp'=135*$2.536*10^{-13}$ F=34.2 pF. Compared to the setup in FIG. 27, the transfer function in the plateau region of a setup according to FIG. 28 would decrease by 41%, taking the original value Cp=50 pF into account.

Figure 29:
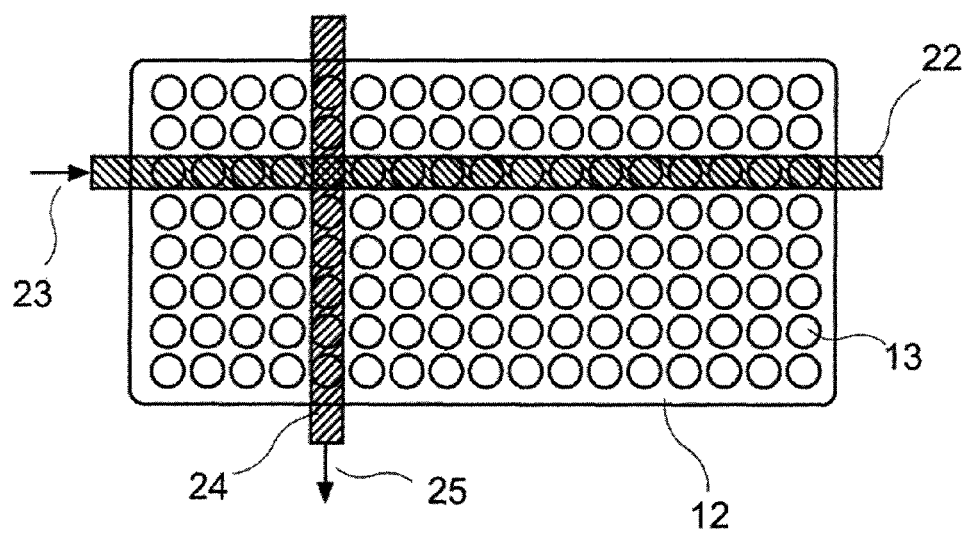
FIG. 29 illustrates a sequence of operation of the dispense volume sensor, in accordance with an embodiment of the invention.

The multiplexed sensor arrangements as shown in FIGS. 26, 27, and 28 utilize multiplexers with a number of channels identical to the number of dispense needles. Multiplexers of reduced channel numbers can be used with a sensor arrangement that is illustrated symbolically in FIG. 29. Here, it is assumed that a multi-well plate has 136 elements, arranged in seventeen columns and eight rows. A demultiplexer with only eight output channels is used to excite one whole row of dispense needles at a time, as indicated in FIG. 29 by incoming arrow 23 and band 22. The simultaneous excitation of all needles in row is achieved by connecting them electrically with each other. A multiplexer with seventeen input channels is used on the detection side to connect all receiving cylinders in one column with the input of the RF voltmeter, as indicated in FIG. 29 by outgoing arrow 25 and band 24. All receiving cylinders in a column are made available to the input of the multiplexer by connecting them electrically in series with each other. At any given time, only one cylinder in a column will receive an RF field, while the remaining seven others represent a parallel capacitance of value $Cp''=7*2.536*10^{-13}$ F=1.8 pF. In operation, a row 22, would be scanned through all columns from left to right. This action results in the read-out of that row. The next row would then be scanned again through all columns from left to right, which results in the read-out of the next row, and so on until the whole array has been read.

Figure 30:
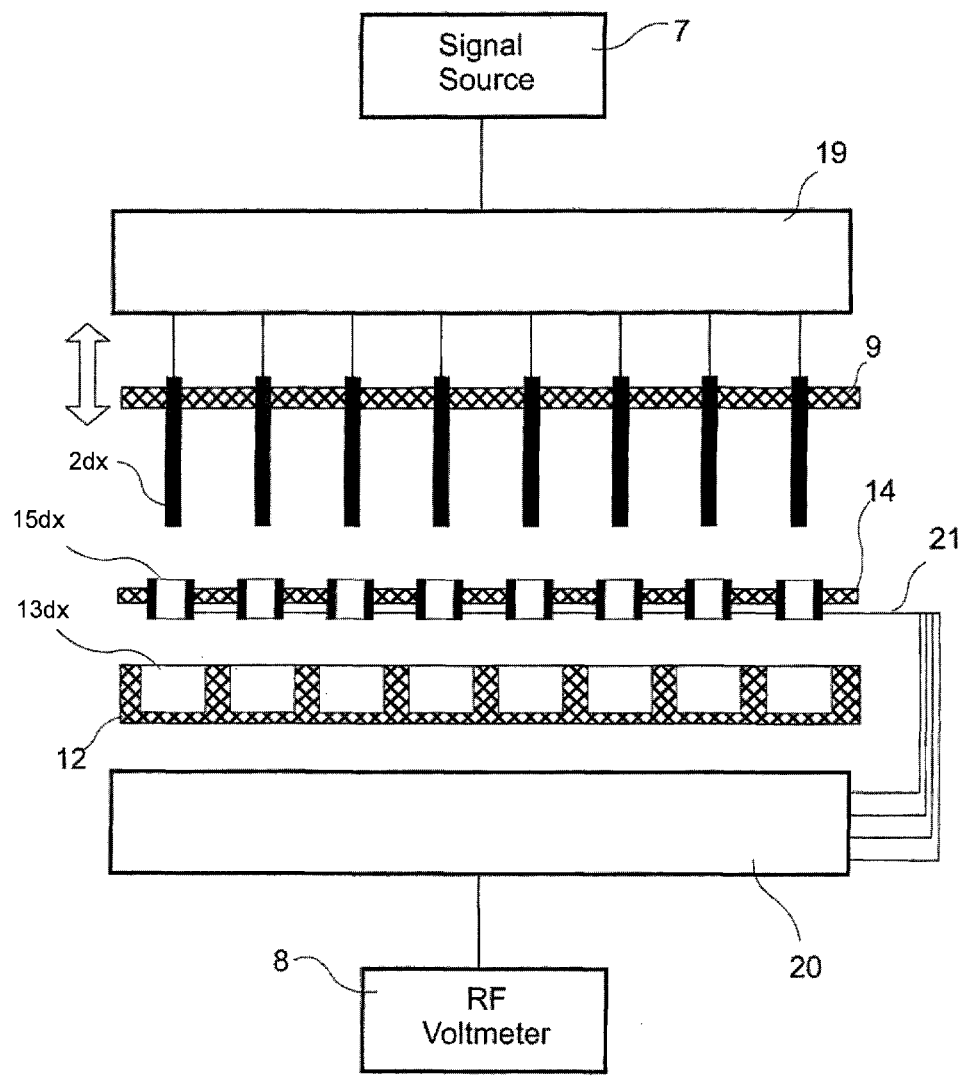
FIG. 30 shows a dispense volume sensor comprising a multiplexed/demultiplexed concentric cylinder capacitor arrangement, in accordance with an embodiment of the invention.

FIG. 30 depicts a multiplexed sensor arrangement corresponding to the embodiment described in FIG. 29, showing a demultiplexer 19 and a multiplexer 20. Receiving cylinders $15d_x$ are insulated from each other and connected with the inputs of the multiplexer 20 through wire harness 21. Both demultiplexer 19 and multiplexer 20 are controlled and synchronized by a common computer, (not shown). The setup of FIG. 30 has the same advantages as the one depicted in FIGS. 27 and 28 in that no detours are required for the array of dispense needles. Additionally, multiplexers of significantly lower channel numbers can be used.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A dispense volume sensor comprising:
   a dispense needle for dispensing a liquid sample; and
   a receiving cylinder for receiving the dispense needle;
   wherein said dispense needle and said receiving cylinder are arranged such that insertion of said dispense needle a certain distance into said receiving cylinder forms a capacitor to detect amounts of liquid located on the outside of said dispense needle after liquid has been aspirated into, or dispensed from, the dispense needle, wherein said dispense needle is made from electrically conducting materials or an outer surface of said dispense needle is electrically conductive.

2. The dispense volume sensor of claim 1, wherein said dispense needle further comprises a needle tip, wherein said dispense needle tip is coaxially received into said receiving cylinder by a certain overlap length.

3. The dispense volume sensor of claim 2, wherein said needle tip is a first electrode and said receiving cylinder is a second electrode.

4. The dispense volume sensor of claim 1, further comprising a processor configured for:

measuring capacitance of said capacitor, and
determining a presence of a lost volume of said dispensed liquid by comparing said measured capacitance value with a calibration capacitance value.

5. The dispense volume sensor of claim 4, wherein the measured capacitance of said capacitor is substantially independent of the dielectric constant of a material that is present on an outside surface of said needle tip.

6. The dispense volume sensor of claim 1, wherein said receiving cylinder is made from electrically conducting materials.

7. The dispense volume sensor of claim 1, wherein an inner surface of said receiving cylinder is electrically conductive.

8. A dispense volume sensor comprising:
   a plurality of dispense needles arranged in an array of at least one row and at least one column held in place by a first electrical insulating member,
   a plurality of receiving cylinders arranged in a matching array of at least one row and at least one column and supported by a second electrical insulating member,
   such that on insertion of said plurality of dispense needles a certain distance into said plurality of receiving cylinders a plurality of capacitors are formed to detect amounts of liquid located on the outside of the respective dispense needles after liquid has been aspirated into, or dispensed from, the respective dispense needles, wherein each of said dispense needles is made from electrically conducting materials or has an outer surface which is electrically conductive.

9. The dispense volume sensor of claim 8, further comprising a signal source connected in parallel with each of said plurality of dispense needles.

10. The dispense volume sensor of claim 8, further comprising;
    a plurality of wells arranged in a matching array to said array of dispense needles, such that each of said dispense needles corresponds to at least one of said plurality of receiving cylinders and at least one of said plurality of said wells.

11. The dispense volume sensor of claim 10, wherein each of said plurality of dispense needles further comprises a needle tip, wherein each said needle tip of said dispense needles has to pass through at least one of said receiving cylinders in order to dispense a liquid into at least one of said plurality of said wells.

12. The dispense volume sensor of claim 8, further comprising;
    a multiplexer having a plurality of input channels and one output channel,
    wherein said plurality of receiving cylinders are connected to said at plurality of input channels of said multiplexer, and said one output channel is connected to an input of a voltmeter.

13. The dispense volume sensor of claim 12, wherein said plurality of receiving cylinders are isolated from each other and individually connected with one of said plurality of inputs of said multiplexer.

14. The dispense volume sensor of claim 8, wherein said plurality of receiving cylinders are connected with each other, and connected with said input of said voltmeter.

15. The dispense volume sensor of claim 8, further comprising;
    a demultiplexer having one input channel and a plurality of output channels,
    wherein said one input channel is connected to an output of a signal source and said plurality of dispense needles are connected to the said plurality of output channels of said demultiplexer.

16. The dispense volume sensor of claim 15, wherein said dispense needles are electrically activated in a series mode by said demultiplexer.

17. The dispense volume sensor of claim 15, wherein said demultiplexer comprises a plurality of output channels equal to the number of dispense needles in said array of dispense needles.

18. The dispense volume sensor of claim 15, wherein said demultiplexer comprises a plurality output channels equal to the number of dispense needles in one row of said array of dispense needles.

19. The dispense volume sensor of claim 8, further comprising;
a demultiplexer having one input and a plurality of outputs, wherein said input of said demultiplexer is connected to an output of a signal source and said plurality of dispense needles are connected to the said plurality of outputs of said demultiplexer; and
a multiplexer having a plurality of inputs and one output, wherein said plurality of receiving cylinders are connected to said plurality of inputs of said multiplexer, and said output of said multiplexer connected to an input of a voltmeter.

20. The dispense volume sensor of claim 19, wherein said dispense needles are electrically activated in a series mode by said demultiplexer.

21. The dispense volume sensor of claim 19, wherein said demultiplexer comprises a plurality of outputs equal to the number of dispense needles in one row of said array of dispense needles.

22. The dispense volume sensor of claim 19, wherein said multiplexer comprises a plurality of inputs equal to the number of receiving cylinders in one column of said array of dispense needles.

23. A method to determine a volume of dispensed liquid comprising:
introducing a target volume of a liquid sample into a dispense needle having a needle tip, said dispense needle being made from electrically conducting materials or an outer surface of said dispense needle being electrically conductive,
dispensing an actual volume of said liquid sample from said dispense needle into a container,
inserting said needle tip into a receiving cylinder a certain distance thereby forming a capacitor to detect amounts of liquid on the outside of said dispense needle,
measuring the capacitance of said capacitor, and
determining the presence of a lost volume of said dispensed liquid sample by comparing said measured capacitance value with a calibration capacitance value.

24. The method of claim 23, wherein said calibration capacitance value is the capacitance value of said capacitor with no liquid sample present on the outside of said dispense needle.

25. The method of claim 23, wherein a greater said measured capacitance value when compared to said calibration capacitance value indicates the presence of said lost volume.

26. The method of claim 23, further comprising:
calculating said lost volume of said dispensed liquid sample by comparing said measured capacitance value with a calibration capacitance value of said capacitor, and
calculating said actual dispensed volume of liquid sample by subtracting said lost volume from said target volume.

27. The method of claim 26, wherein a processor is used to calculate said lost volume and said actual dispensed volume.

28. The method of claim 23, wherein said step of introducing a target volume of a liquid sample into a dispense needle further comprising the steps of:
inserting said needle tip of said dispense needle into said liquid sample, and
aspirating said target volume of said liquid sample into said dispense needle.

29. The method of claim 23, wherein said step of measuring the capacitance of said capacitor further comprising the steps of:
applying an input signal to said dispense needle from a signal source, and
measuring the output signal from said receiving cylinder using a voltmeter.

30. The method of claim 23, wherein said measured capacitance value is substantially independent of the dielectric constant of said liquid sample.

31. The method of claim 23 wherein said capacitor is a concentric cylinder capacitor.

32. The method of claim 23, wherein said comparison of said measured capacitance value with a calibration capacitance value is carried out by a processor.

33. The method of claim 29, wherein said input signal is a time-dependent electrical signal.

34. The method of claim 33, wherein said time-dependent signal is a sine-wave signal.

35. The method of claim 34, wherein the frequency of said sine-wave signal is selected so that the transfer function of the electrical circuit becomes frequency-independent.

36. The method of claim 34, wherein said said-wave signal is free of frequency stabilization.

* * * * *